United States Patent
Waight et al.

(10) Patent No.: US 11,938,194 B2
(45) Date of Patent: Mar. 26, 2024

(54) CYSTEINE MUTATED ANTIBODIES FOR CONJUGATION

(71) Applicant: SEAGEN INC., Bothell, WA (US)

(72) Inventors: Andrew Waight, Bothell, WA (US); Chris Leiske, Bothell, WA (US); Travis Biechele, Bothell, WA (US); Django Sussman, Bothell, WA (US); Patrick Burke, Bothell, WA (US); Jocelyn Leiske, Bothell, WA (US)

(73) Assignee: SEAGEN INC., Bothell, WA (US)

( * ) Notice: Subject to any disclaimer, the term of this patent is extended or adjusted under 35 U.S.C. 154(b) by 998 days.

(21) Appl. No.: 16/483,025

(22) PCT Filed: Feb. 28, 2018

(86) PCT No.: PCT/US2018/020206
§ 371 (c)(1),
(2) Date: Aug. 1, 2019

(87) PCT Pub. No.: WO2018/160683
PCT Pub. Date: Sep. 7, 2018

(65) Prior Publication Data
US 2022/0175947 A1 Jun. 9, 2022

Related U.S. Application Data

(60) Provisional application No. 62/465,129, filed on Feb. 28, 2017, provisional application No. 62/561,151, filed on Sep. 20, 2017.

(51) Int. Cl.
*A61K 47/68* (2017.01)
*C07K 16/18* (2006.01)

(52) U.S. Cl.
CPC ...... *A61K 47/6829* (2017.08); *A61K 47/6851* (2017.08); *A61K 47/6889* (2017.08); *C07K 16/18* (2013.01); *C07K 2317/524* (2013.01)

(58) Field of Classification Search
None
See application file for complete search history.

(56) References Cited

U.S. PATENT DOCUMENTS

| | | | |
|---|---|---|---|
| 5,219,996 A | 6/1993 | Bodmer et al. |
| 5,624,821 A | 4/1997 | Winter et al. |
| 5,677,425 A | 10/1997 | Bodmer et al. |
| 6,165,745 A | 12/2000 | Ward et al. |
| 6,491,916 B1 | 12/2002 | Bluestone et al. |
| 6,528,624 B1 | 3/2003 | Idusogie et al. |
| 6,737,056 B1 | 5/2004 | Presta et al. |
| 7,097,840 B2 | 8/2006 | Erickson et al. |
| 7,276,585 B2 | 10/2007 | Lazar et al. |
| 7,297,775 B2 | 11/2007 | Dusogie et al. |
| 7,332,581 B2 | 2/2008 | Presta et al. |
| 7,491,390 B2 | 2/2009 | Law et al. |
| 7,498,298 B2 | 3/2009 | Doronina et al. |
| 7,521,541 B2 | 4/2009 | Eigenbrot et al. |
| 7,855,275 B2 | 12/2010 | Eigenbrot et al. |
| 7,964,406 B2 | 6/2011 | Spits et al. |
| 7,968,687 B2 | 6/2011 | McDonagh et al. |
| 8,242,252 B2 | 8/2012 | McDonagh et al. |
| 8,455,622 B2 * | 6/2013 | McDonagh ........ A61K 47/6849 530/391.1 |
| 8,722,857 B2 | 5/2014 | Chen et al. |
| 9,061,074 B2 | 6/2015 | Carter et al. |
| 9,518,118 B2 | 12/2016 | Chen et al. |
| 9,688,762 B2 | 6/2017 | Igawa et al. |
| 10,017,577 B2 | 7/2018 | Polakis et al. |
| 10,328,084 B2 | 6/2019 | Jeffrey et al. |
| 10,407,505 B2 | 9/2019 | Carter et al. |
| 2004/0132101 A1 | 7/2004 | Lazer et al. |
| 2005/0037000 A1 | 2/2005 | Stavenhagen et al. |
| 2005/0064514 A1 | 3/2005 | Stavenhagen et al. |
| 2006/0024298 A1 | 2/2006 | Lazar et al. |
| 2006/0083736 A1 | 4/2006 | Law et al. |
| 2006/0134709 A1 | 6/2006 | Stavenhagen et al. |
| 2006/0235208 A1 | 10/2006 | Lazar et al. |
| 2007/0009523 A1 | 1/2007 | Presta |
| 2007/0053901 A1 | 3/2007 | Lazar et al. |

(Continued)

FOREIGN PATENT DOCUMENTS

| AU | 2005286607 B2 | 3/2006 |
|---|---|---|
| CA | 2580141 C | 12/2013 |

(Continued)

OTHER PUBLICATIONS

Jeffrey et al., Biorganic & Medicinal Chemistry Letters 17: 2278-2280 (Year: 2007).*
Lloyd et al., Protein Engineering, Design & Selection 22:159-168 (Year: 2009).*
Edwards et al., J Mol Biol 334(1): 103-118 (Year: 2003).*
Piche-Nicholas et al., MABS 10(1): 81-94 (Year: 2018).*
Armour et al., "Recombinant human IgG molecules lacking Fcγ receptor 1 binding and monocyte triggering activities," Eur. J. Immunol., 29:2613-2624, (1999).
Burke et al., "Development of Novel Quaternary Ammonium Linkers for Antibody-Drug Conjugates," Mol Cancer Ther, 15(5):938-945, (2016).

(Continued)

*Primary Examiner* — Phuong Huynh
(74) *Attorney, Agent, or Firm* — Alston & Bird LLP

(57) ABSTRACT

The invention provides modified heavy chain constant regions including a cysteine at position 295 by EU numbering and optionally at position 239 by EU numbering. These cysteine residues provide sites for conjugation to a drug or label. When both cysteines are present in a normal heterodimeric antibody format, there are four such sites per molecule of antibody allowing a stoichiometry of one molecule of antibody to four of drug or label. Selection of the cysteine at position 295 with or without cysteine at position 239 is advantageous over cysteines at many other positions due to ease of expression, stability and cytotoxicity.

15 Claims, 14 Drawing Sheets
Specification includes a Sequence Listing.

(56) References Cited

U.S. PATENT DOCUMENTS

| | | | |
|---|---|---|---|
| 2007/0092940 A1 | 4/2007 | Eigenbrot et al. | |
| 2007/0224188 A1 | 9/2007 | Allan et al. | |
| 2007/0269369 A1 | 11/2007 | Gegg et al. | |
| 2008/0095766 A1 | 4/2008 | Koenig et al. | |
| 2008/0131435 A1 | 6/2008 | Stavenhagen et al. | |
| 2008/0138349 A1 | 6/2008 | Stavenhagen et al. | |
| 2008/0154025 A1 | 6/2008 | Lazar et al. | |
| 2008/0161541 A1 | 7/2008 | Lazar et al. | |
| 2008/0227958 A1 | 9/2008 | Thompson et al. | |
| 2008/0248028 A1 | 10/2008 | Lazar et al. | |
| 2008/0317758 A9 | 12/2008 | Presta | |
| 2010/0104564 A1* | 4/2010 | Hansen | C07K 16/2878 435/71.1 |
| 2010/0158909 A1 | 6/2010 | McDonagh et al. | |
| 2012/0294853 A1 | 11/2012 | McDonagh et al. | |
| 2013/0028919 A1 | 1/2013 | Howard et al. | |
| 2013/0209458 A1 | 8/2013 | Goletz et al. | |
| 2013/0309223 A1 | 11/2013 | Sutherland et al. | |
| 2014/0086942 A1 | 3/2014 | Carter et al. | |
| 2015/0050269 A1 | 2/2015 | Igawa et al. | |
| 2015/0147316 A1 | 5/2015 | Sutherland et al. | |
| 2015/0165064 A1* | 6/2015 | Bregeon | A61K 31/5517 435/68.1 |
| 2015/0166654 A1 | 6/2015 | Igawa et al. | |
| 2015/0353630 A1 | 12/2015 | Igawa et al. | |
| 2016/0051695 A1* | 2/2016 | Lin | A61K 47/6889 424/179.1 |
| 2016/0067351 A1* | 3/2016 | Geierstanger | A61K 47/6817 435/69.6 |
| 2016/0068613 A1 | 3/2016 | Regula et al. | |
| 2016/0074527 A1* | 3/2016 | Flygare | C07K 16/28 540/496 |
| 2016/0130358 A1* | 5/2016 | Bhakta | C07K 16/32 530/391.5 |
| 2016/0229915 A1 | 8/2016 | Igawa et al. | |
| 2017/0021033 A1 | 1/2017 | Geierstanger et al. | |
| 2017/0114151 A1 | 4/2017 | Dimasi et al. | |
| 2017/0121421 A1 | 5/2017 | Cortez et al. | |
| 2017/0216452 A1 | 8/2017 | Ma et al. | |
| 2017/0274092 A1 | 9/2017 | Chen et al. | |
| 2017/0291955 A1 | 10/2017 | Li et al. | |
| 2017/0362318 A1 | 12/2017 | Crowley et al. | |
| 2018/0057598 A1 | 3/2018 | Lazar et al. | |
| 2018/0057607 A1 | 3/2018 | Gawa et al. | |
| 2018/0155451 A1 | 6/2018 | Mimoto et al. | |

FOREIGN PATENT DOCUMENTS

| | | | | |
|---|---|---|---|---|
| CN | 101065151 B | 12/2014 | | |
| EP | 2011870 A1 | 1/2009 | | |
| EP | 2176295 A1 | 4/2010 | | |
| EP | 2762166 A1 | 8/2014 | | |
| EP | 2925778 A1 | 10/2015 | | |
| EP | 3191518 A1 | 7/2017 | | |
| EP | 3310813 A1 | 4/2018 | | |
| EP | 1141024 B1 | 8/2018 | | |
| JP | 2009-95249 A | 5/2009 | | |
| JP | 5427348 B2 | 2/2014 | | |
| WO | WO 1989/001974 A1 | 3/1989 | | |
| WO | WO 2003/074679 A2 | 9/2003 | | |
| WO | WO 2004/042017 A2 | 5/2004 | | |
| WO | WO 2004/073656 A2 | 9/2004 | | |
| WO | WO 2005/018572 A2 | 3/2005 | | |
| WO | WO 2006/034488 A2 | 3/2006 | | |
| WO | WO 2006/074397 A2 | 7/2006 | | |
| WO | WO 2006/104989 A2 | 10/2006 | | |
| WO | WO 2006/105062 A2 | 10/2006 | | |
| WO | WO 2006/105338 A2 | 10/2006 | | |
| WO | WO 2008/113909 A2 | 10/2006 | | |
| WO | WO-2006104989 A2 * | 10/2006 | | C07K 14/70535 |
| WO | WO 2006/116260 A2 | 11/2006 | | |
| WO | WO 2007/022070 A2 | 2/2007 | | |
| WO | WO 2008/020827 A2 | 2/2008 | | |
| WO | WO 2008/052187 A2 | 5/2008 | | |
| WO | WO 2008/070593 A2 | 6/2008 | | |
| WO | WO 2011/005481 A1 | 1/2011 | | |
| WO | WO 2012/125850 A1 | 9/2012 | | |
| WO | WO 2013/047748 A1 | 4/2013 | | |
| WO | WO 2015/157592 A1 | 10/2015 | | |
| WO | WO 2015/157595 A1 | 10/2015 | | |
| WO | WO 2016/040684 A1 | 3/2016 | | |
| WO | WO 2016/040724 A1 | 3/2016 | | |
| WO | WO 2016/203432 A1 | 12/2016 | | |
| WO | WO 2017/104783 A1 | 6/2017 | | |
| WO | WO 2017/196764 A1 | 11/2017 | | |
| WO | WO 2018/009811 A1 | 1/2018 | | |
| WO | WO 2018/069375 A1 | 4/2018 | | |
| WO | WO 2018/142322 A1 | 8/2018 | | |
| WO | WO 2018/148447 A1 | 8/2018 | | |

OTHER PUBLICATIONS

Burton et al., "Molecular Recognition of Antibody (IgG) by Cellular Fc Receptor (FcRI)," Molecular Immunology, 25(11):1175-1181, (1988).

Caron et al., "Engineered humanized dimeric forms of IgG are more effective antibodies," J. Exp. Med., 176:1191-1195, (1992).

Crivianu-Gaita et al., "High efficiency reduction capability for the formation of Fab' antibody fragments from F(ab)2 units," Biochemistry and Biophysics Reports, 2:23-28, (2015).

Denny, "DNA minor groove alkylating agents," Exp. Opin. Ther. Patents, 10(4): 459-474, (2000).

Excerpt from the file history of EP 1141024 B1, published Aug. 8, 2018, entitled "Polypeptide Comprising a Variant Human IgG1 Fc Region", 218 pages.

Harada et al., "Hinge Region of Human IgG2 Protein: Conformational Studies with Monoclonal Antibodies," Molecular Immunology, 29(2):145-149, (1992).

Hengel et al., "Measurement of in Vivo Drug Load Distribution of Cysteine-Linked Antibody-Drug Conjugates Using Microscale Liquid Chromatography Mass Spectrometry," Anal. Chem., 86:3420-3425, (2004).

Hutchins et al., "Improved biodistribution, tumor targeting, and reduced immunogenicity in mice with a y4 variant of 3ampath-1H," Proc. Natl. Acad. Sci. USA, 92:11980-11984, (1995).

Jefferis et al., "Molecular Definition of Interaction Sites on Human IgG FOR Fc Receptors (huFcy R)," Molecular Immunology, 27(12):1237-1240, (1990).

Junutula et al., "Site-specific conjugation of a cytotoxic drug to an antibody improves the therapeutic index," Nature Biotechnology, 26(8):925-932, (2008).

Levengood et al., "Orthogonal Cysteine Protection Enables Homogeneous Multi-Drug Antibody-Drug Conjugates," Angew. Chem. Int. Ed., 56:733-737, (2017).

Leverett et al., "Design, Synthesis, and Cytotoxic Evaluation of Novel Tubulysin Analogs as ADC Payloads," ACS Med. Chem. Lett., 7 pages, doi: 10.1021/acsmedchemlett.6b002, (2016).

Loke et al., "Mylotarg has potent anti-leukaemic effect: a systematic review and meta-analysis of anti-CD33 antibody treatment in acute myeloid leukaemia," Ann. Hematol, 94:361-373, (2015).

Lyon et al., "Conjugation of Anticancer Drugs Through Endogenous Monoclonal Antibody Cysteine Residues," Methods in Enzymology, 502:123-138, (2012).

Lyons et al., "Site-specific attachment to recombinant antibodies via introduced surface cysteine residues," Protein Eng., 3:703-708, (1990).

McDonagh et al., "Engineered anti-CD70 antibody-drug conjugate with increased therapeutuc index," Mal. Cancer There., 7:2913-2923, (2008).

Morgan et al., "The N-terminal end of the CH2 domain of chimeric human IgG1 anti-HLA-DR is necessary for Clq, FcyRI and FcyRIII binding," Immunology, 86:319-324, (1995).

Pan et al., "Conformation and Dynamics of Interchain Cysteine-Linked Antibody-Drug Conjugates as Revealed by Hydrogen/Deuterium Exchange Mass Spectrometry," Anal. Chem., 86:2657-2664, (2014).

(56) References Cited

OTHER PUBLICATIONS

Raghavan et al., "Fc Receptors and their Interactions with Immunoglobulins," Annu. Rev. Cell Dev. Biol., 12:181-220, (1996).
Renard et al., "Deriving Topological Constraints from Functional Data for the Design of Reagentless Fluorescent Immunosensors," J. Mol. Biol., 326:167-175, (2003).
Schott et al., "Preparation, Characterization, and in Vivo Biodistribution Properties of Synthetically Cross-Linked Multivalent Antitumor Antibody Fragments," Bioconjugate Chem., 4:153-165, (1993).
Shen et al., "Conjugation site modulates the in vivo stability and therapeutic activity of antibody-drug conjugates," Nature Biotechnology, 30(2):184-191, doi:10.1038/nbt.2108, (2012).
Shopes, "A genetically engineered human IgG mutant with enhanced cytolytic activity," J. Immunol., 148:2918-2922, (1992).
Shopes, "A genetically engineered human IgG with limited flexibility fully initiates cytolysis via complement," Mol. Immunol., 30:603-609, (1993).
Sondermann et al., "Molecular Basis for Immune Complex Recognition: A Comparison of Fc-Receptor Structures," J. Mol. Biol., 309:737-749, (2001).
Stavenhagen et al., "Fc optimization of the therapeutic antibodies enhances their ability to fill tumor cells in vitro and controls tumor expansion in viva via low-affinity activating Fcγ receptors," Cancer Res., 67:8882-8890, (2007).
Stimmel et al., "Site-specific conjugation an serine—cysteine variant monolconal antibodies," J. Biol. Chem., 275:30445-30450, (2000).
Sussman et al., "Engineered Cysteine Antibodies: Improved Antibody-Drug conjugate Vehicles," Poster presentation pf Abstract No. B204, 102nd annual Meeting of the American Association for Cancer Research, Orlando, FL., Apr. 2-6, 2011.
Sussman et al., "Abstract 4634: Engineered cysteine drug conjugates show potency and improved safety," Cancer Res, In: Proceedings of the 103rd Annual Meeting of the American Association for Cancer Research, Abstract No. 4634, doi:1538-7445.AM2012-4634, (2012).
Sussman et al., "Engineered cysteine antibodies: an improved antibody-drug conjugate platform with a novel mechanism of drug-linker stability," Protein Engineering, Design & Selection, 31(2):47-54, (2017).
Sutherland et al., "Lysosomal Trafficking and Cysteine Protease Metabolism Confer Target-specific Cytotoxicity by Peptide-linked Anti-CD30-Auristatin Conjugates," Journal of Biological Chemistry, 281(15):10540-10547, (2006).
Tamm et al., "IgG Binding Sites on Human Fc-γ Receptors," Intern. Rev. Immunol., 16:57-85, (1997).
Tumey et al., "Optimization of Tubulysin Antibody-Drug Conjugates: A Case Study in Addressing ADC Metabolism," ACS Med. Chem. Lett., 7:977-982, doi: 10.1021/acsmedchemlett.6b00195, (2016).
Unkeless et al., "Human Fc Receptors for IgG," Intern. Rev. Immunol., 5:165-171, (1989).
Valliere-Douglass et al., "Approaches to Interchain Cysteine-Linked ADC Characterization by Mass Spectrometry," Mol. Pharmaceutics, 12:1774-1783, (2015).
Valliere-Douglass et al., "Native Intact Mass Determination of Antibodies Conjugated with Monomethyl Auristatin E and F at Interchain Cysteine Residues," Anal. Chem., 84:2843-2849, (2012).

Vitetta et al., "Considering Therapeutic Antibodies," Science, 313:308-309, (2006).
Voynov et al., "Design and Application of Antibody Cysteine Variants," Bioconjugate Chem., 21:385-392, (2010).
Waight et al., "Title," AACR, Abstract No. 8111, Seattle Genetics, 1 page, (2017).
U.S. Appl. No. 12/516,914, Final Office Action dated Sep. 24, 2012.
U.S. Appl. No. 12/516,914, Non-Final Office Action dated Apr. 23, 2012.
U.S. Appl. No. 12/516,914, Notice of Allowance dated Dec. 11, 2012.
U.S. Appl. No. 12/516,914, Requirement for Restriction/Election dated Nov. 29, 2011.
U.S. Appl. No. 13/826,007, Final Office Action dated Feb. 10, 2016.
U.S. Appl. No. 13/826,007, Non-Final Office Action dated Sep. 11, 2015.
U.S. Appl. No. 13/826,007, Requirement for Restriction/Election dated May 22, 2015.
U.S. Appl. No. 13/826,260, Final Office Action dated Feb. 6, 2015.
U.S. Appl. No. 13/826,260, Non-Final Office Action dated Sep. 18, 2014.
U.S. Appl. No. 13/826,260, Notice of Allowance dated Feb. 18, 2015.
U.S. Appl. No. 15/189,216, Notice of Allowance dated Apr. 23, 2019.
U.S. Appl. No. 15/189,216, Requirement for Restriction/Election dated May 17, 2018.
WIPO Application No. PCT/US2007/086205, PCT International Preliminary Report on Patentability dated Jun. 3, 2009.
WIPO Application No. PCT/US2007/086205, PCT International Search Report completed Jul. 28, 2008.
WIPO Application No. PCT/US2007/086205, PCT Written Opinion of the International Searching Authority completed Jul. 28, 2008.
WIPO Application No. PCT/US2018/020206, PCT International Preliminary Report on Patentability dated Oct. 12, 2016.
WIPO Application No. PCT/US2018/020206, PCT Written Opinion of the International Searching Authority dated May 4, 2018.
Goldmacher, et al., "Antibody-drug conjugates: using onoclonal antibodies for delivery of cytotoxic payloads to cancer cells," Therapeutic Delivery, 2(3), 397-416, (2011).
Jackson, et al., "Using the Lessons learned From the Clinic to Improve the Preclinical Development of Antibody Drug Conjugates," Pharm Res, 32:3458-3469, (2015).
Jeffrey, et al., "A Potent Anti-CD70 Antibody-Drug Conjugate Combining a Dimeric Pyrrolobenzodiazepine Drug with Site-Specific Conjugation Technology," Bioconjugate Chem, 4, 1256-1263, (2013).
Kim, et al., "Strategies and Advancement in Antibody-Drug Conjugate Optimization for Targeted Cancer Therapeutics," Biomol Ther, 23(6), 493-509, (2015).
Li, et al., "A Biparatopic HER2-Targeting Antibody-Drug Conjugate Induces Tumor Regression in Primary Models Refractory to or Ineligible for HER2-Targetied Therapy," Cancer Cell 29, 117-129, (Jan. 11, 2016).
Thompson, et al., "Rational design, biophysical and biological characterization of site-specific antibody-tubulysin cojugates with improved stability, efficacy and pharmacokinetics," Journal of Controlled Release, 236, 100-116, (2016).
EP 18760842.7 Extended European Search Report dated Nov. 24, 2020.

\* cited by examiner

SEQUENCE LISTING

<160> NUMBER OF SEQ ID NOS: 22

<210> SEQ ID NO 1
<211> LENGTH: 330
<212> TYPE: PRT
<213> ORGANISM: Artificial sequence
<220> FEATURE:
<223> OTHER INFORMATION: Synthesized

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 326
<212> TYPE: PRT
<213> ORGANISM: Artificial sequence
<220> FEATURE:
<223> OTHER INFORMATION: Synthesized

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 3
<211> LENGTH: 377
<212> TYPE: PRT
<213> ORGANISM: Artificial sequence
<220> FEATURE:
<223> OTHER INFORMATION: Synthesized

<400> SEQUENCE: 3

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 4
<211> LENGTH: 327
<212> TYPE: PRT
<213> ORGANISM: Artificial sequence
<220> FEATURE:
<223> OTHER INFORMATION: Synthesized

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 5
<211> LENGTH: 330
<212> TYPE: PRT
<213> ORGANISM: Artificial sequence
<220> FEATURE:
<223> OTHER INFORMATION: Synthesized

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Cys Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 6
<211> LENGTH: 326
<212> TYPE: PRT
<213> ORGANISM: Artificial sequence
<220> FEATURE:
<223> OTHER INFORMATION: Synthesized

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Cys Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 7
<211> LENGTH: 377
<212> TYPE: PRT
<213> ORGANISM: Artificial sequence
<220> FEATURE:
<223> OTHER INFORMATION: Synthesized

<400> SEQUENCE: 7

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

-continued

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
        180                 185                 190

Val Val Asp Val Ser His Glu Asp Pro Glu Val Gln Phe Lys Trp Tyr
    195                 200                 205

Val Asp Gly Val Glu Val His Asn Ala Lys Thr Lys Pro Arg Glu Glu
210                 215                 220

Cys Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 8
<211> LENGTH: 327
<212> TYPE: PRT
<213> ORGANISM: Artificial sequence
<220> FEATURE:
<223> OTHER INFORMATION: Synthesized

<400> SEQUENCE: 8

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

-continued

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Cys Phe
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
    195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 9
<211> LENGTH: 330
<212> TYPE: PRT
<213> ORGANISM: Artificial sequence
<220> FEATURE:
<223> OTHER INFORMATION: Synthesized

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Cys Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

```
Glu Cys Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 10
<211> LENGTH: 326
<212> TYPE: PRT
<213> ORGANISM: Artificial sequence
<220> FEATURE:
<223> OTHER INFORMATION: Synthesized

<400> SEQUENCE: 10

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Cys Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Cys Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205
```

```
Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 11
<211> LENGTH: 377
<212> TYPE: PRT
<213> ORGANISM: Artificial sequence
<220> FEATURE:
<223> OTHER INFORMATION: Synthesized

<400> SEQUENCE: 11

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Cys Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Cys Tyr Asn Ser Thr Phe Arg Val Val Ser Val Leu Thr Val Leu His
225                 230                 235                 240
```

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 12
<211> LENGTH: 327
<212> TYPE: PRT
<213> ORGANISM: Artificial sequence
<220> FEATURE:
<223> OTHER INFORMATION: Synthesized

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Cys Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Cys Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 13
<211> LENGTH: 330
<212> TYPE: PRT
<213> ORGANISM: Artificial sequence
<220> FEATURE:
<223> OTHER INFORMATION: Synthesized

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Cys Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

<210> SEQ ID NO 14
<211> LENGTH: 326
<212> TYPE: PRT
<213> ORGANISM: Artificial sequence
<220> FEATURE:
<223> OTHER INFORMATION: Synthesized

<400> SEQUENCE: 14

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Cys Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

```
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 15
<211> LENGTH: 377
<212> TYPE: PRT
<213> ORGANISM: Artificial sequence
<220> FEATURE:
<223> OTHER INFORMATION: Synthesized

<400> SEQUENCE: 15

Ala Ser Thr Lys Gly Pro Ser Val Phe Pro Leu Ala Pro Cys Ser Arg
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Thr Cys Asn Val Asn His Lys Pro Ser Asn Thr Lys Val Asp Lys
                85                  90                  95
Arg Val Glu Leu Lys Thr Pro Leu Gly Asp Thr Thr His Thr Cys Pro
            100                 105                 110
Arg Cys Pro Glu Pro Lys Ser Cys Asp Thr Pro Pro Cys Pro Arg
        115                 120                 125
Cys Pro Glu Pro Lys Ser Cys Asp Thr Pro Pro Cys Pro Arg Cys
    130                 135                 140
Pro Glu Pro Lys Ser Cys Asp Thr Pro Pro Cys Pro Arg Cys Pro
145                 150                 155                 160
Ala Pro Glu Leu Leu Gly Gly Pro Ser Val Phe Leu Phe Pro Pro Lys
                165                 170                 175
Pro Lys Asp Thr Leu Met Ile Ser Arg Thr Pro Glu Val Thr Cys Val
            180                 185                 190
Val Val Asp Val Ser His Glu Asp Pro Glu Val Gln Phe Lys Trp Tyr
        195                 200                 205
Val Asp Gly Val Glu Val His Asn Ala Lys Thr Lys Pro Arg Glu Cys
    210                 215                 220
Gln Tyr Asn Ser Thr Phe Arg Val Val Ser Val Leu Thr Val Leu His
225                 230                 235                 240
Gln Asp Trp Leu Asn Gly Lys Glu Tyr Lys Cys Lys Val Ser Asn Lys
                245                 250                 255
Ala Leu Pro Ala Pro Ile Glu Lys Thr Ile Ser Lys Thr Lys Gly Gln
            260                 265                 270
Pro Arg Glu Pro Gln Val Tyr Thr Leu Pro Pro Ser Arg Glu Glu Met
        275                 280                 285
Thr Lys Asn Gln Val Ser Leu Thr Cys Leu Val Lys Gly Phe Tyr Pro
    290                 295                 300
Ser Asp Ile Ala Val Glu Trp Glu Ser Ser Gly Gln Pro Glu Asn Asn
305                 310                 315                 320
```

```
Tyr Asn Thr Thr Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
        370                 375

<210> SEQ ID NO 16
<211> LENGTH: 327
<212> TYPE: PRT
<213> ORGANISM: Artificial sequence
<220> FEATURE:
<223> OTHER INFORMATION: Synthesized

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Cys Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 17
<211> LENGTH: 330
<212> TYPE: PRT
<213> ORGANISM: Artificial sequence
<220> FEATURE:
<223> OTHER INFORMATION: Synthesized

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Cys Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

```
Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 18
<211> LENGTH: 326
<212> TYPE: PRT
<213> ORGANISM: Artificial sequence
<220> FEATURE:
<223> OTHER INFORMATION: Synthesized

<400> SEQUENCE: 18

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Cys Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Cys Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 19
<211> LENGTH: 377
<212> TYPE: PRT
<213> ORGANISM: Artificial sequence
<220> FEATURE:
<223> OTHER INFORMATION: Synthesized

<400> SEQUENCE: 19

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Cys Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Cys
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350
```

Phe Ser Cys Ser Val Met His Glu Ala Leu His Asn Arg Phe Thr Gln
                355                 360                 365

Lys Ser Leu Ser Leu Ser Pro Gly Lys
    370                 375

<210> SEQ ID NO 20
<211> LENGTH: 327
<212> TYPE: PRT
<213> ORGANISM: Artificial sequence
<220> FEATURE:
<223> OTHER INFORMATION: Synthesized

<400> SEQUENCE: 20

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Cys Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Cys Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

```
<210> SEQ ID NO 21
<211> LENGTH: 26
<212> TYPE: PRT
<213> ORGANISM: Artificial sequence
<220> FEATURE:
<223> OTHER INFORMATION: Synthesized

<400> SEQUENCE: 21

Thr His Thr Cys Pro Pro Cys Pro Ala Pro Glu Leu Leu Gly Gly Pro
1               5                   10                  15

Cys Val Phe Leu Phe Pro Pro Lys Pro Lys
            20                  25

<210> SEQ ID NO 22
<211> LENGTH: 29
<212> TYPE: PRT
<213> ORGANISM: Artificial sequence
<220> FEATURE:
<223> OTHER INFORMATION: Synthesized

<400> SEQUENCE: 22

Thr Lys Pro Arg Glu Glu Cys Tyr Asn Ser Thr Tyr Arg Val Val Ser
1               5                   10                  15

Val Leu Thr Val Leu His Gln Asp Trp Leu Asn Gly Lys
            20                  25
```

CYSTEINE MUTATED ANTIBODIES FOR CONJUGATION

CROSS-REFERENCE TO RELATED APPLICATIONS

The present application is a national stage entry of PCT/US2018/020206 filed Feb. 28, 2018, which claims the benefit of 62/465,129 filed Feb. 28, 2017 and 62/561,151 filed Sep. 20, 2017, each of which is incorporated by reference in its entirety for all purposes.

REFERENCE TO A SEQUENCE LISTING

The application includes a txt sequence listing named 534948SEQLST.TXT of 61,164 bytes and created Aug. 1, 2019 incorporated by reference.

BACKGROUND

The heavy chain constant region of antibodies has been subject to numerous mutations to achieve various effects. These effects include increasing or decreasing effector function, increasing or decreasing stability or half-life, increasing or decreasing posttranslational modification, and providing sites for conjugation. S239C has been described as a site for conjugation but by itself permits loading of only two molecules of drug in antibody of two heavy and two light chains. Different sites for conjugation may vary in suitability depending on accessibility to a conjugation reagent, expression and glycosylation pattern of the antibody, and stability on storage, in vivo half-life and cytotoxicity of the antibody drug conjugate.

SUMMARY OF THE CLAIMED INVENTION

The invention provides an antibody or fusion protein comprising a heavy chain constant region in which position 295 by EU numbering is occupied by cysteine. Optionally, the antibody or fusion protein is conjugated to a drug or label via the cysteine at position 295. Optionally, position 239 by EU numbering is occupied by a cysteine. Optionally, the antibody or fusion protein is conjugated to a drug or label via the cysteines at positions 295 and 239.

In another embodiment, the antibody or fusion protein is conjugated to a drug or label via the cysteine at position 294 by EU numbering. Optionally, position 239 by EU numbering is occupied by a cysteine.

The invention further provides an antibody as a heterodimer comprising two heavy chains and two light chains, wherein one molecule of the antibody is conjugated to four molecules of the drug via conjugation to the cysteine at position 295 and 239 in both heavy chains. Optionally, the constant region has an isotype, which is human IgG1, IgG2, IgG3 or IgG4.

The invention further provides an antibody as a heterodimer comprising two heavy chains and two light chains, wherein one molecule of the antibody is conjugated to four molecules of the drug via conjugation to the cysteine at position 294 and 239 in both heavy chains. Optionally, the constant region has an isotype, which is human IgG1, IgG2, IgG3 or IgG4.

In some antibodies or fusion proteins, the drug is a tubulysin. Optionally, the drug is conjugated to the antibody via a glucuronide linker. Optionally, the antibody is conjugated to a compound having a structure shown below providing the tubulysin and glucuronide linker.

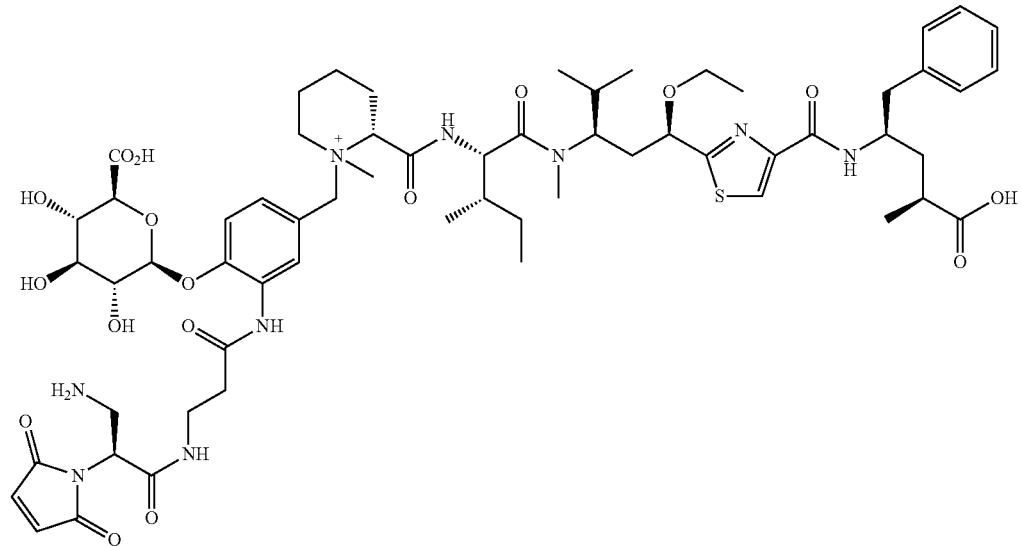

-continued

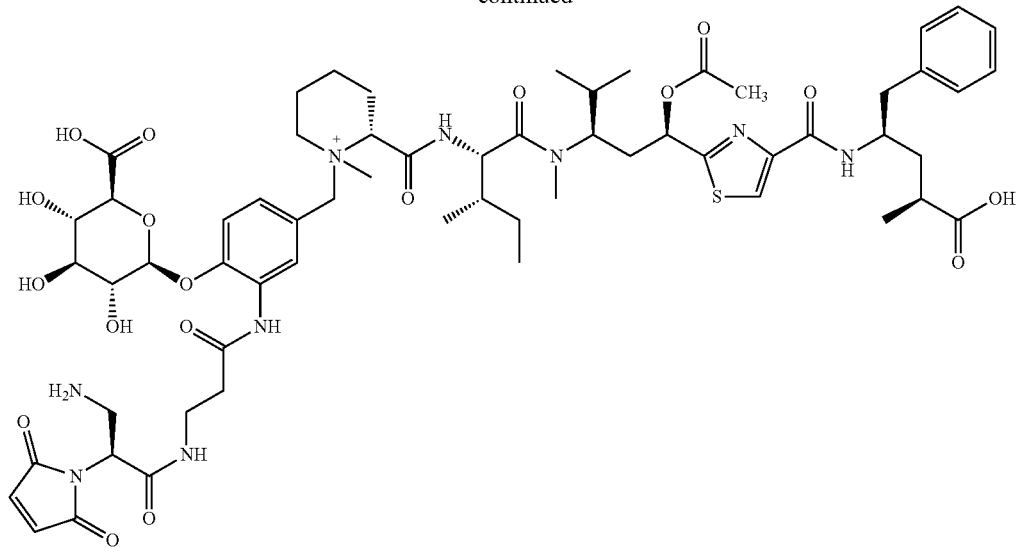

Optionally the drug is MMAE, MMAF, or a minor groove binder, or a PBD. Optionally, the heavy chain constant region has the sequence of any of SEQ ID NOS. 5-12 provided the C-terminal lysine can be absent.

Optionally, the antibody or fusion protein is conjugated to the drug via a cleavable linker.

The invention further provides a pharmaceutical composition comprising an antibody or fusion protein as described above.

The invention further provides an antibody or fusion protein comprising a heavy chain constant region in which position 239 by EU numbering is occupied by cysteine, which cysteine is conjugated to tubulysin M.

The invention further provides a method of producing an antibody or fusion protein comprising a heavy chain constant region in which positions 239 and 295 by EU numbering are occupied by cysteines. The method comprises culturing a cell engineered to encode the antibody or fusion protein, wherein the antibody or fusion protein is expressed; and purifying the antibody or fusion protein. Optionally, the method further comprises conjugating the antibody or fusion protein to a drug via the cysteines at position 239 and 295. Optionally, the method further comprises contacting the antibody with a reducing agent that inhibits formation of disulfide bonds between cysteines at positions 239 and 295. Optionally, the antibody or fusion protein is contacted with the reducing agent by including the reducing agent in a medium in which the antibody or fusion protein is cultured. Optionally, the reducing agent is dithiothreitol, beta-mercaptoethanol or tris(2-carboxyethyl)phosphine. Optionally, the reducing agent is dithiothreitol at a concentration of 0.1 to 2 mM.

BRIEF DESCRIPTIONS OF DRAWINGS

Figure 6:
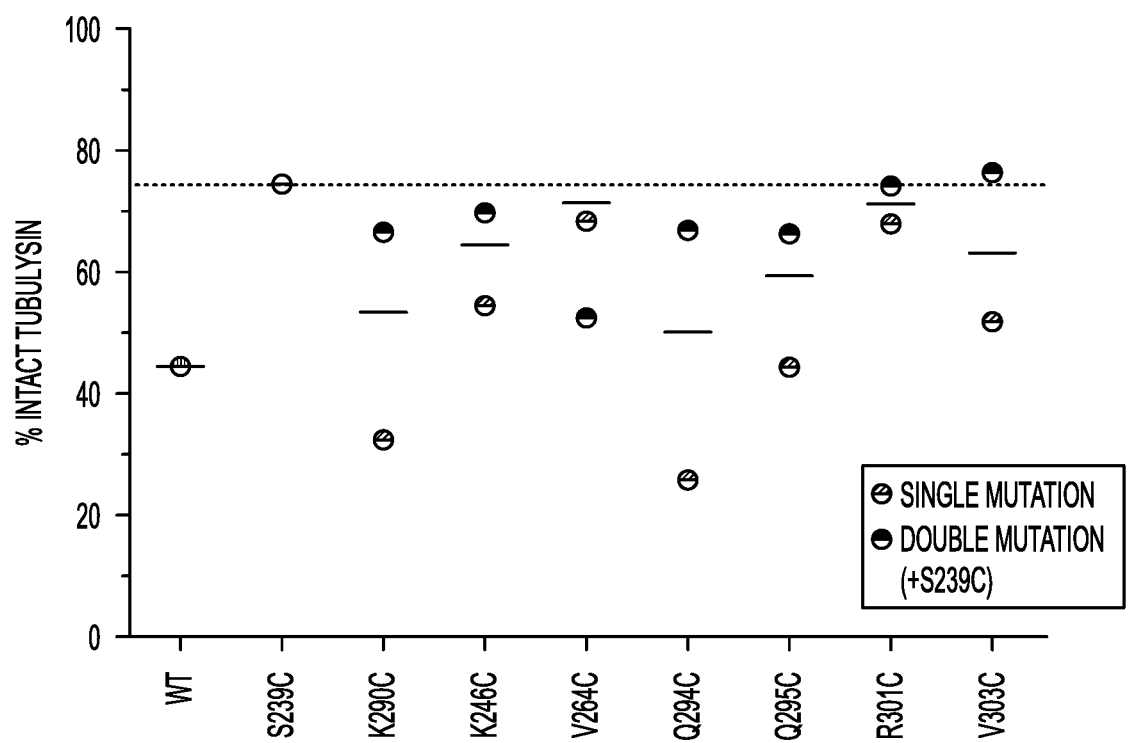

FIG. 6 also shows tubulysin stability.

Figure 7:
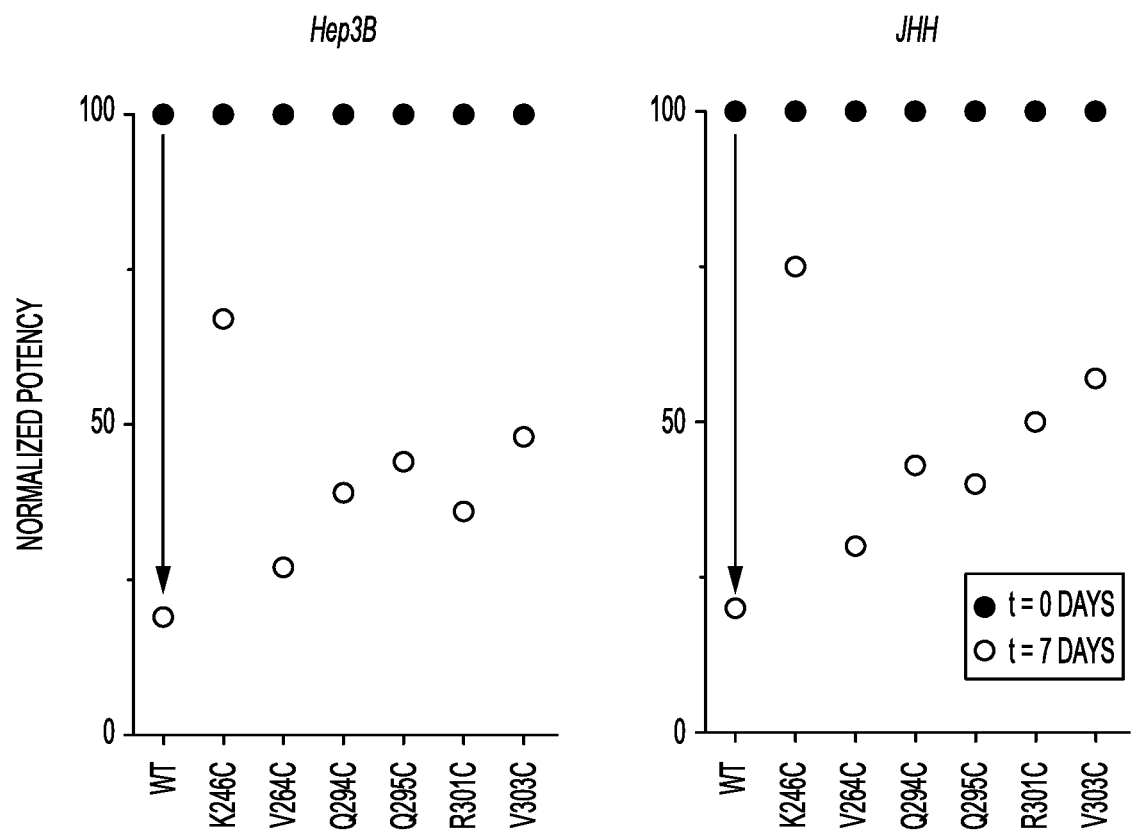

FIG. 7 shows differences in cytotoxicity after subjecting ADCs with double mutations to rat plasma.

Figure 8:
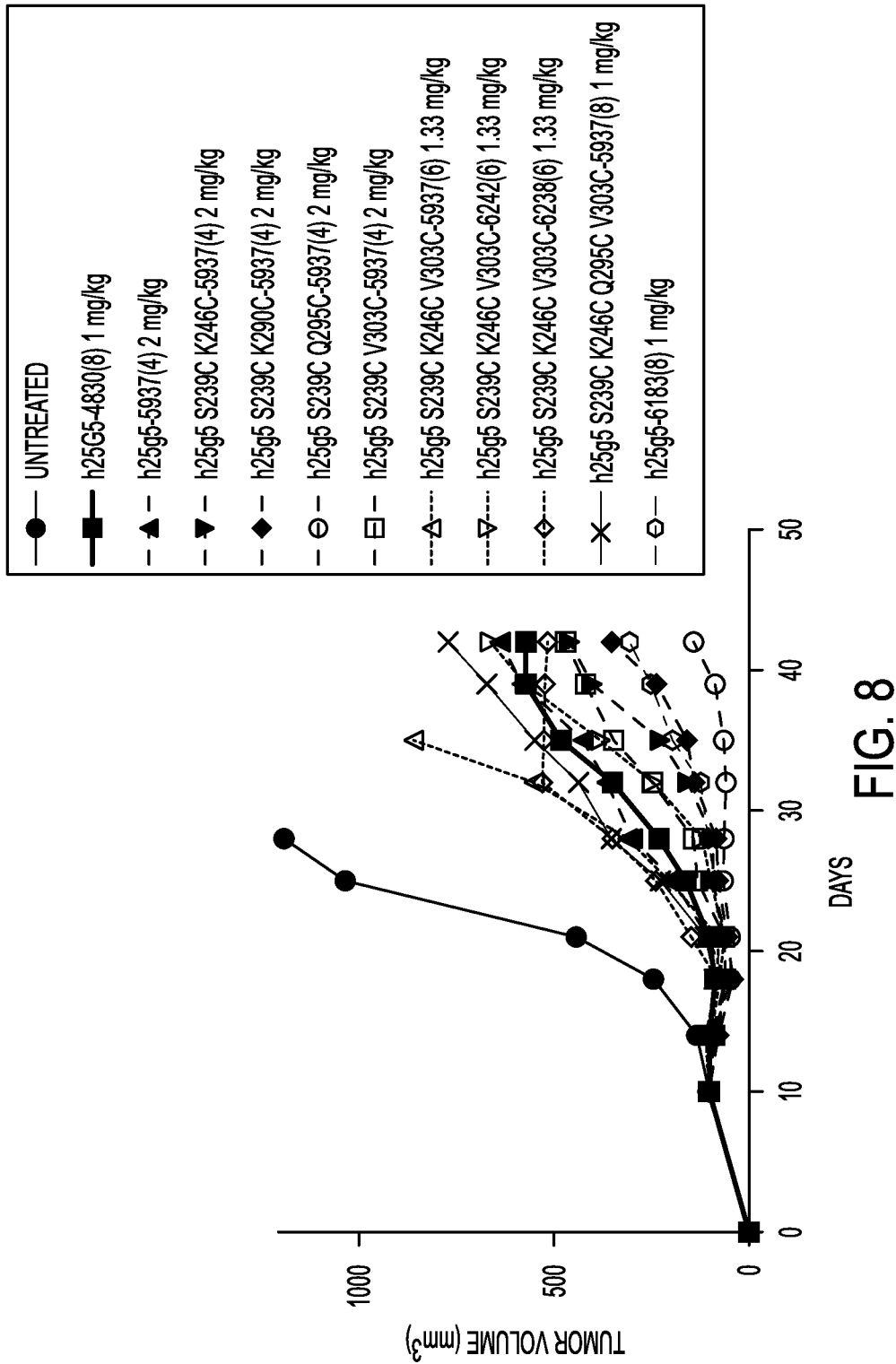
Figure 9:
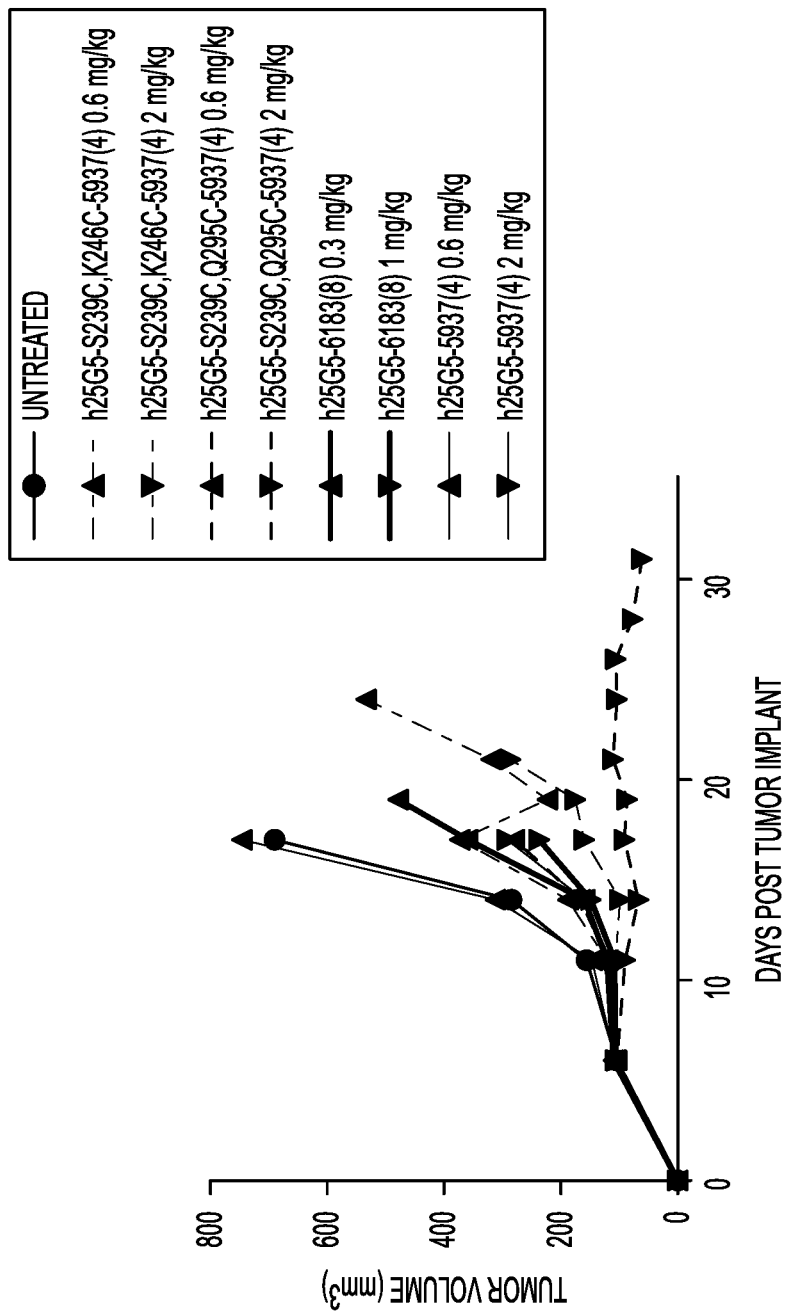

FIGS. 8 and 9 compare various antibody drug conjugates in tumor xenograft models.

Figure 10A:
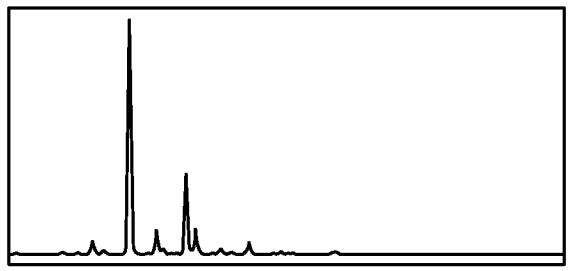
Figure 10C:
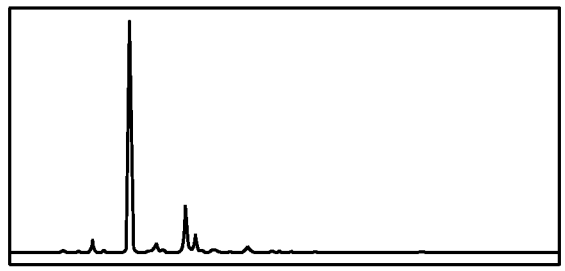
Figure 10B:
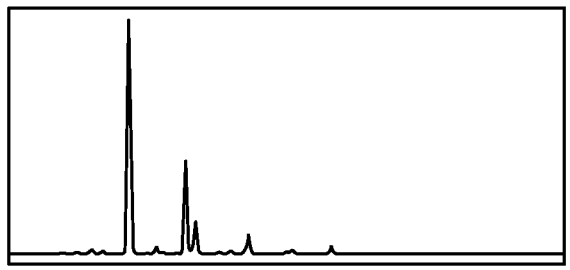
Figure 10D:
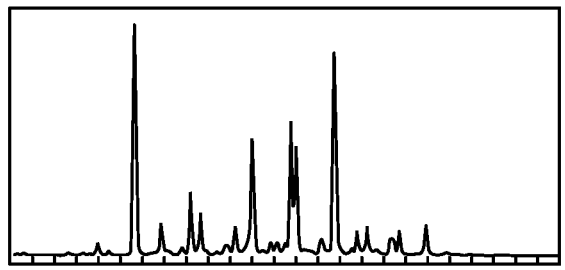
Figure 11:
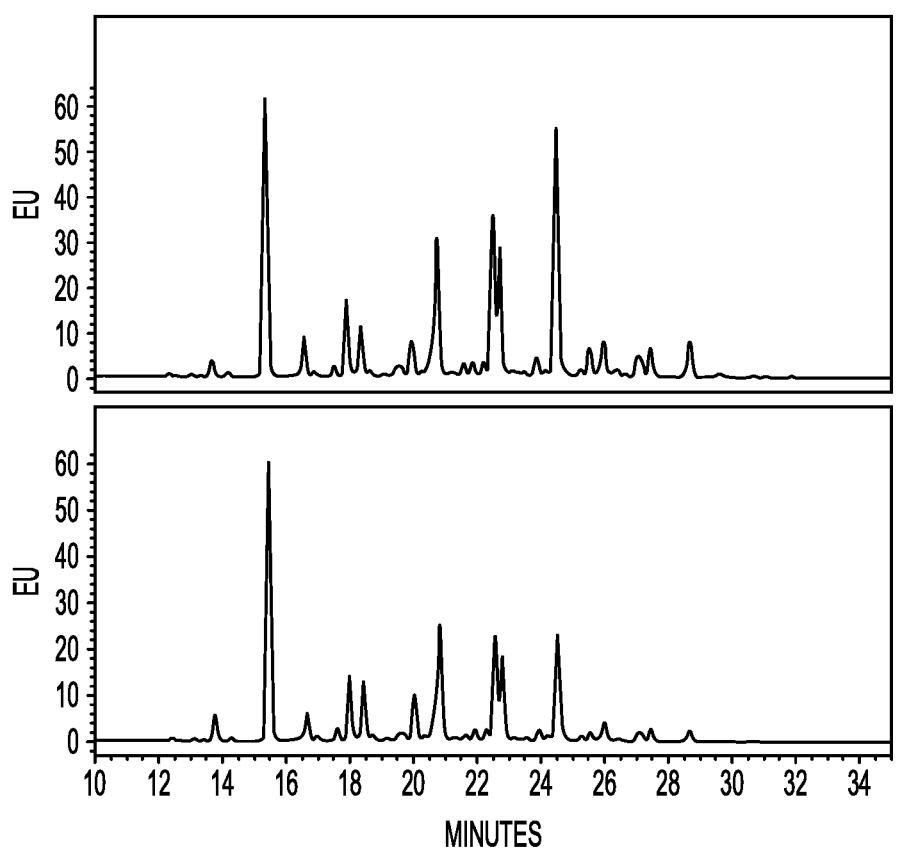

FIG. 10A Typical IgG1 glycosylation pattern, FIG. 10B S239C mutation glycosylation pattern, FIG. 10C Q295C glycosylation pattern, FIG. 10D S239C/Q295C double mutation glycosylation pattern FIG. 11: (Top) Glycosylation pattern for stable expression mAb with S239C/Q295C mutation (Bottom) Transient expression mAb with S239C/Q295C mutation.

Figure 12:
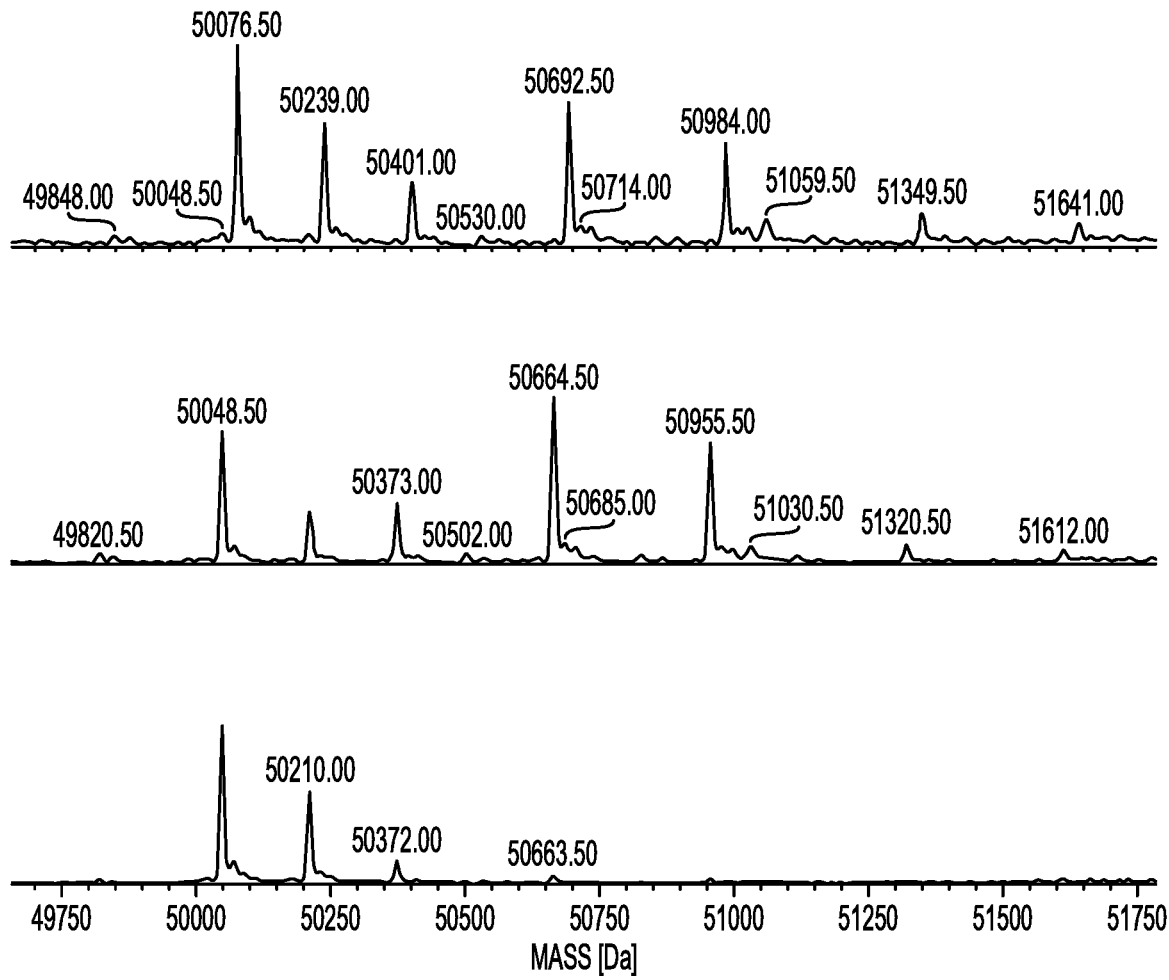

FIG. 12: PLRP-MS analysis of glycan patter of (Top) S239C/E294C mutant mAb, (Middle) S239C/Q295C mutant mAb and (Bottom) wild type glycan.

Figure 13:
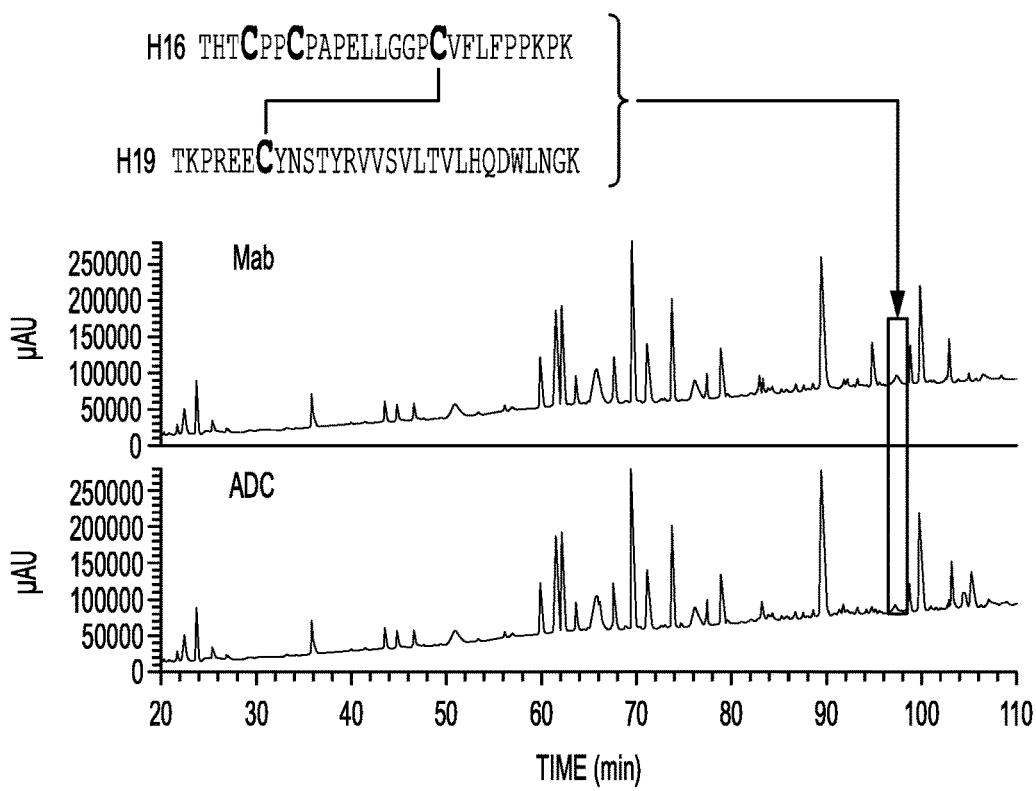

FIG. 13: Non-reduced peptide map showing H16 (S239C) (SEQ ID NO:21) and H19 (Q295C) (SEQ ID NO:22) covalently bound together in parental mAb.

Figure 14:
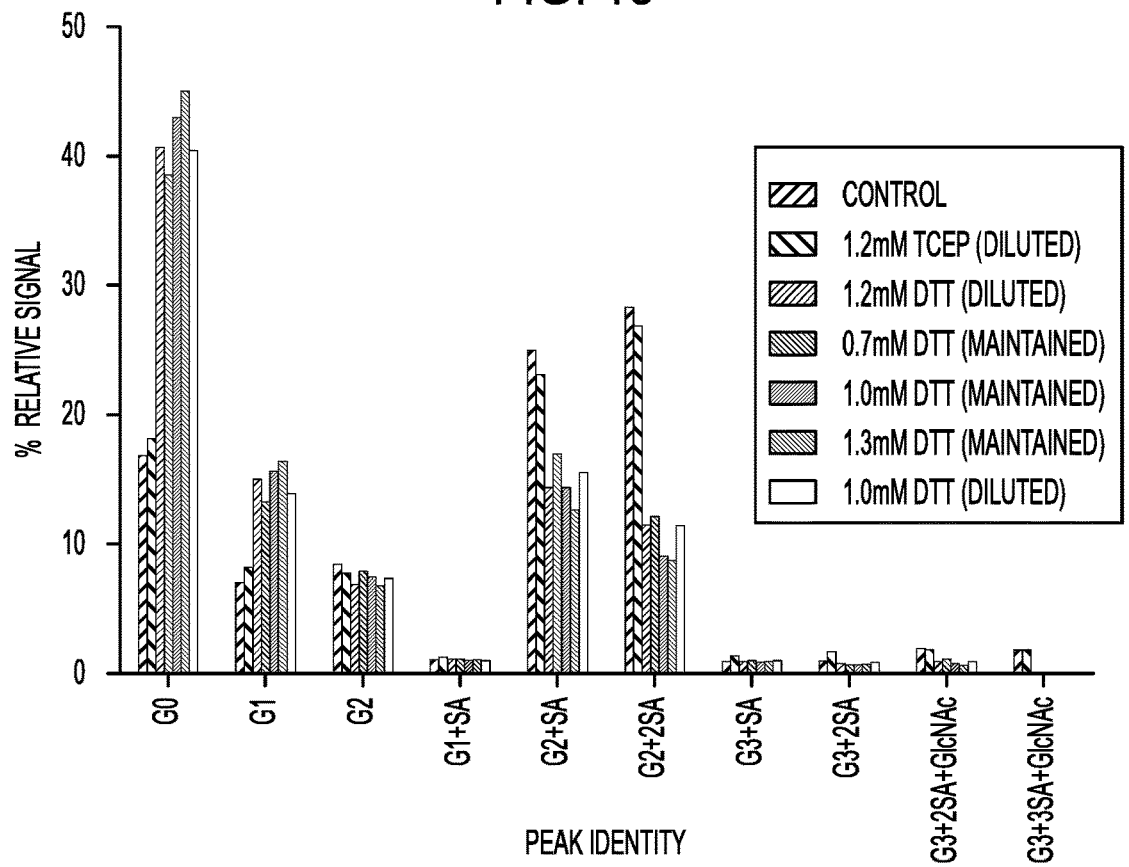

FIG. 14: Stable expression data comparing various DTT and tris(2-carboxyethyl)phosphine (TCEP) concentration in cell media and the produced glycans using the S239C/Q295C mutant.

Figure 15:
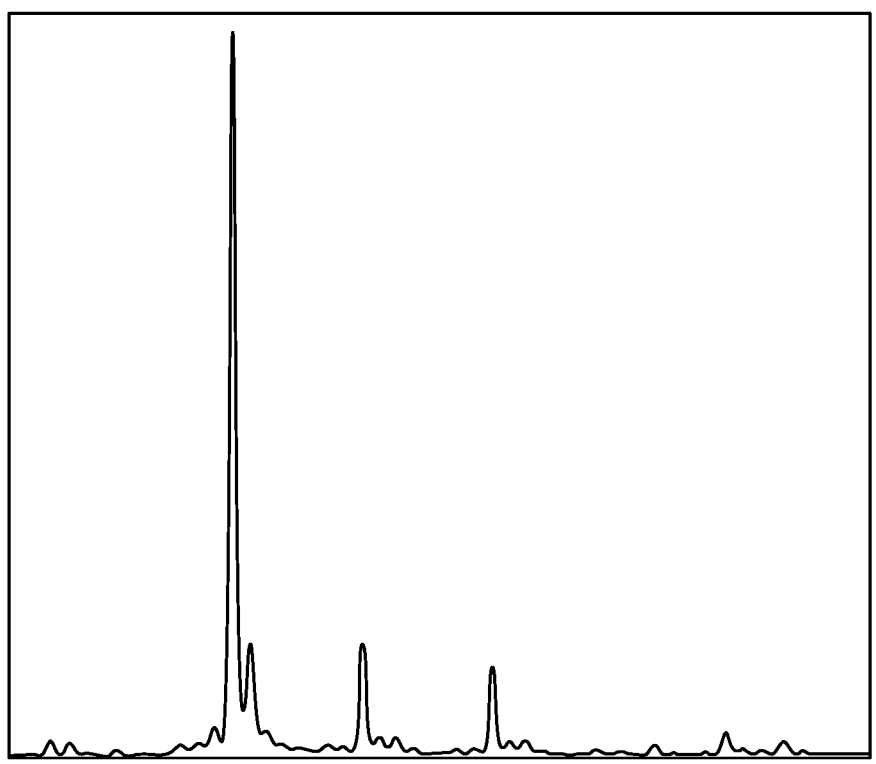

FIG. 15: Glycan analysis of transiently expressed S239C/Q295C mutant when cultured in maintained 1.2 mM dithiothreitol (DTT).

DEFINITIONS

An isolated antibody or ADC is typically at least 50% w/w pure of interfering proteins and other contaminants arising from its production or purification but does not exclude the possibility that the antibody is combined with an excess of pharmaceutical acceptable carrier(s) or other vehicle intended to facilitate its use. Sometimes antibodies or ADCs are at least 60%, 70%, 80%, 90%, 95 or 99% w/w pure of interfering proteins and contaminants from production or purification.

Specific binding of an antibody alone or as a component of an ADC to its target antigen means an affinity of at least $10^6$, $10^7$, $10^8$, $10^9$, or $10^{10}$ M$^{-1}$. Specific binding is detectably higher in magnitude and distinguishable from nonspecific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

The basic antibody structural unit is a tetramer of subunits. Each tetramer includes two pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region is a light chain variable region without the light chain signal peptide. The carboxy-terminal portion of each chain defines a constant region. The heavy chain constant region is primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989, Ch. 7, incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chains or between different light chains are assigned the same number.

The term "antibody" includes intact antibodies and binding fragments thereof. Typically, antibody fragments compete with the intact antibody from which they were derived for specific binding to the target including separate heavy chains, light chains Fab, Fab', F(ab')$_2$, F(ab)c, diabodies, Dabs, nanobodies, and Fv. Fragments can be produced by recombinant DNA techniques, or by enzymatic or chemical separation of intact immunoglobulins. The term "antibody" also includes a diabody (homodimeric Fv fragment) or a minibody ($V_L$—$V_H$—$C_H3$), a bispecific antibody or the like. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)). The term "antibody" includes an antibody by itself (naked antibody) or an antibody conjugated to a cytotoxic or cytostatic drug.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with sequences maximally aligned.

Sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of matched and mismatched positions not counting gaps in the window of comparison (i.e., the window size), and multiplying the result by 100 to yield the percentage of sequence identity. Antibody sequences are aligned by the Kabat numbering convention such that residues occupying the same numbered position are aligned. After alignment, if a subject sequence is compared with a reference sequence, the percentage sequence identity between the subject and reference sequences is the number of positions occupied by the same amino acid in both the subject and reference sequences divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

Designation of a range of values includes all integers within or defining the range.

An antibody effector function refers to a function contributed by an Fc domain(s) of an Ig. Such functions can be, for example, antibody-dependent cellular cytotoxicity, antibody-dependent cellular phagocytosis or complement-dependent cytotoxicity. Such function can be effected by, for example, binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of the targeted cell. Fc regions of antibodies can recruit Fc receptor (FcR)-expressing cells and juxtapose them with antibody-coated target cells. Cells expressing surface FcR for IgGs including FcγRIII (CD16), FcγRII (CD32) and FcγRIII (CD64) can act as effector cells for the destruction of IgG-coated cells. Such effector cells include monocytes, macrophages, natural killer (NK) cells, neutrophils and eosinophils. Engagement of FcγR by IgG activates antibody-dependent cellular cytotoxicity (ADCC) or antibody-dependent cellular phagocytosis (ADCP). ADCC is mediated by $CD16^+$ effector cells through the secretion of membrane pore-forming proteins and proteases, while phagocytosis is mediated by $CD32^+$ and $CD64^+$ effector cells (see *Fundamental Immunology*, 4th ed., Paul ed., Lippincott-Raven, N.Y., 1997, Chapters 3, 17 and 30; Uchida et al., 2004, *J. Exp. Med.* 199:1659-69; Akewanlop et al., 2001, *Cancer Res.* 61:4061-65; Watanabe et al., 1999, *Breast Cancer Res. Treat.* 53:199-207). In addition to ADCC and ADCP, Fc regions of cell-bound antibodies can also activate the complement classical pathway to elicit complement-dependent cytotoxicity (CDC). C1q of the complement system binds to the Fc regions of antibodies when they are complexed with antigens. Binding of C1q to cell-bound antibodies can initiate a cascade of events involving the protease activation of C4 and C2 to generate the C3 convertase. Cleavage of C3 to C3b by C3 convertase enables the activation of terminal complement components including C5b, C6, C7, C8 and C9. Collectively, these proteins form membrane-attack complex pores on the antibody-coated cells. These pores disrupt the cell membrane integrity, killing the target cell (see *Immunobiology*, $6^{th}$ ed., Janeway et al., Garland Science, N. Y., 2005, Chapter 2).

A "cytotoxic effect" refers to the depletion, elimination and/or the killing of a target cell. A "cytotoxic agent" refers to an agent that has a cytotoxic effect on a cell. Cytotoxic agents can be conjugated to an antibody or administered in combination with an antibody.

A "cytostatic effect" refers to the inhibition of cell proliferation. A "cytostatic agent" refers to an agent that has a cytostatic effect on a cell, thereby inhibiting the growth and/or expansion of a specific subset of cells. Cytostatic agents can be conjugated to an antibody or administered in combination with an antibody.

The term "pharmaceutically acceptable" means approved or approvable by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an antibody or ADC is combined.

The phrase "pharmaceutically acceptable salt," refers to pharmaceutically acceptable organic or inorganic salts of an antibody or conjugate thereof or agent administered with an antibody. Exemplary salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Unless otherwise apparent from the context, the term "about" encompasses values within a standard deviation of a stated value.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. Nos. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having its CDRs, preferably as defined by Kabat, entirely or substantially from a donor antibody and variable region framework sequences and constant regions, if present, entirely or substantially from human antibody sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

A chimeric antibody is an antibody in which the mature variable regions of light and heavy chains of a non-human antibody (e.g., a mouse) are combined with human or nonhuman primate light and heavy chain constant regions. Such antibodies substantially or entirely retain the binding specificity of the mouse antibody, and are about two-thirds human or non-human primate sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

An antibody-drug conjugate (ADC) comprises an antibody conjugated to a drug. A drug is a compound known or suspected to have pharmacological activity, usually cytotoxic or cytostatic activity.

When an antibody component of an antibody drug conjugate is said to include cysteine at position 239 and/or 295 or at position 239 and/or 294 what is meant is that the antibody includes cysteine before conjugation to the drug in the conjugate. In the conjugate, the cysteine is derivatized via bonding of its sulfhydryl group to a drug or linker.

When an antibody is said to be conjugated to a drug, linkage can be direct or indirect via one or more linking moieties.

DETAILED DESCRIPTION

I. General

The invention provides modified heavy chain constant regions including a cysteine at position 294 or 295 by EU numbering and optionally at position 239 by EU numbering. These cysteine residues provide sites for conjugation to a drug or label. When two cysteines are present per heavy chain in a normal heterodimeric antibody format, there are four such sites per molecule of antibody allowing a stoichiometry of one molecule of antibody to four of drug or label. Selection of the cysteine at position 294 or 295 with or without cysteine at position 239 is advantageous over cysteines at many other positions due to ease of expression, stability and cytotoxicity. The invention also provides modified heavy chain constant regions including a cysteine at position 295 by EU numbering conjugated to tubulysin M.

Cysteines at position 239, 294 and 295 are particularly advantageous for conjugation to hydrophobic drugs such as tubulysin or PBDs. Although practice of the invention is not dependent on an understanding of mechanism, it is believed that glycosylation proximate to such conjugation sites masks the hydrophobic moieties increasing their stability and half-life.

II. Heavy Chain Constant Regions

Exemplary wildtype sequences of human IgG1, IgG2, IgG3 and IgG4 are provided as SEQ ID NOS. 1-4. Preferred constant regions of the invention have the sequence of SEQ ID NO. 1, 2, 3 or 4 except that position 295 is occupied by cysteine (SEQ ID NOS. 5-8 respectively) or position 295 and position 239 are occupied by cysteine (SEQ ID NOS. 9-12 respectively). Other preferred constant regions of the invention have the sequence of SEQ ID NO:1, 2, 3, or 4 except that position 294 is occupied by cysteine (SEQ ID NOS: 13-16 respectively) or positions 294 and 239 are occupied by cysteine (SEQ ID NOS. 17-20 respectively).

A constant region is considered to be of a designated isotype if it differs from that isotype by no more than 1, 2, 3, 4, 5, 6, 7, 8, 9 or 10 substitutions, deletions or internal insertions, except however, that the CH1 domain can be omitted entirely as can the upper hinge region. Variations from the designated SEQ ID Nos. can represent one or several natural allotypic or isoallotypic variations, variations to increase or reduce an effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004), for which exemplary substitutions include a Gln at position 250 and/or a Leu at position 428 (EU numbering. Other variations can add or remove sites of post-translational modification, such as N-linked glycosylation at N-X-S/T motifs. Variations can also include introduction of knobs (i.e., replacement of one or more amino acids with larger amino acids) or holes (i.e., replacement of one or more amino acids with smaller amino acids) to promote formation of heterodimers between different heavy chains for production of bispecific antibodies. Exemplary substitutions to form a knob and hole pair are T336Y and Y407T respectively (Ridgeway et al., Protein Engineering vol. 9 no. 7 pp. 617-621, 1996). One or more residues from the C-terminus of constant regions, particularly a C-terminal lysine on the heavy chain, can be lost as a result of post-translational modification.

Modified constant regions and antibodies or fusion proteins incorporating such constant regions are preferably characterized by ease of expression, stability, reduced glycosylation, accessibility to conjugation, and substantially unchanged effector functions and affinity for antigen. That is, the binding affinity is typically the same within experimental error or at least within a factor of 2 or 3 of a suitable control antibody with an isotype-matched wild type constant region. The same is the case for effector functions.

Immunogenicity of modified constant regions or antibodies or fusion proteins incorporated modified constant regions compared with isotype matched controls can be assessed in vitro from dendrite maturation or T-cell proliferation on challenge (Gaitonde et al., Methods Mol. Biol. 2011; 716: 267-80) or in vivo by comparing incidence of reactive antibodies against administered antibodies between populations. The immunogenicity of modified constant regions or antibodies or fusion proteins incorporating the modified constant regions is preferably not significantly different from the isotype matched controls or not worse than 2, 3, or 5 fold greater than the isotype matched control.

III. Antibodies and Fusion Proteins

The modified heavy chain constant regions described above can be incorporated into antibodies or fusion proteins. For example, for expression of a bivalent monospecific antibody, a modified heavy chain constant region is expressed fused to a heavy chain variable region and together with a light chain including a light chain variable region and a light chain constant region. The heavy and light chain bind to one another via the CH1 region of the heavy chain and light chain constant region to a form a heterodimer. Two heterodimers then pair by association of hinge, CH2 and CH3 regions of the IgG heavy chain to form a tetramer unit, as is the case for a conventional antibody. For expression of a bispecific antibody, a modified heavy constant region is expressed fused to each of two heavy chain variable regions of different target specificities. The heavy chains can each assembly with a co-expressed light chain and the heavy chain-light chain complexes form heterodimers in which both heavy chains are present. The light chain variable regions can be the same (see e.g., US 20100331527A1) or different within a unit.

The modified constant regions can be used with any type of engineered antibody including chimeric, humanized, veneered or human antibodies. The antibody can be a monoclonal antibody or a genetically engineered polyclonal antibody preparation (see U.S. Pat. No. 6,986,986).

For fusion protein proteins, a modified constant region is expressed linked to a heterologous polypeptide. A heterologous polypeptide in a fusion protein is a polypeptide not naturally linked to an immunoglobulin constant region. Such a polypeptide can be a full-length protein or any fragment thereof of sufficient length to retain specific binding to the antigen bound by the full-length protein. For example, a heterologous polypeptide can be a receptor extracellular domain or ligand thereto. The heterologous polypeptide provides a binding region at the N-terminus of the constant region and is sometimes referred to simply as a binding region. The IgG CH1 region is not typically included in the constant region for fusion proteins. The hinge region or portion thereof, particularly the upper hinge region is sometimes omitted or replaced by a synthetic linker peptide. Exemplary receptor proteins whose extracellular domains can be combined with modified heavy chain constant regions of the invention include TNF-alpha receptor ECD, LFA-3 ECD, CTLA-4 ECD, IL-1R1 ECD, TPO mimetic, VEGFR1 or VEGFR2 ECD.

IV. Antibody Expression

Nucleic acids encoding antibody chains or fusion proteins can be made by solid state synthesis, PCR amplification of overlapping oligonucleotide fragments or site-directed mutagenesis of existing nucleic acids. Such nucleic acids are expressed in an expression vector. Vectors can be configured to encode a modified heavy chain constant region and/or human light chain constant region such that they can be expressed as fusions with inserted heavy chain and light chain variable regions or a heterologous polypeptide.

The origin of replication and expression control elements (promoter, enhancer, signal peptide and so forth) in a vector can be configured for use in different cell types, such as bacteria, yeast or other fungi, insect cells, and mammalian cells. Mammalian cells are a preferred host for expressing nucleotide segments encoding antibodies or fusion proteins of the invention (see Winnacker, From Genes to Clones, (VCH Publishers, N Y, 1987)). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. Preferably, the cells are nonhuman. Preferably, an antibody or fusion protein of the invention is expressed from a monoclonal cell line.

Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Cells are transfected with one or more vectors encoding the antibody or fusion protein to be expressed. For a multi-chain antibody, the heavy and light chains can be expressed on the same or separate vectors. For expression of multi-specific complexes, the DNA encoding the components of the complexes (i.e., different antibodies or fusion proteins) can be on the same or different vectors.

Antibody or fusion protein chains are expressed, processed to remove signal peptides, assembled and secreted from host cells. Antibodies or fusion proteins can be purified from cell culture supernatants by conventional antibody purification methods. If the hybrid constant region includes an IgG portion, then the purification can include a chromatography step using protein A or protein G as the affinity reagent. Conventional antibody purification procedures, such as ion exchange, hydroxyapatite chromatograph or HPLC can also be used (see generally, Scopes, Protein Purification (Springer-Verlag, NY, 1982)).

In some methods, antibodies or fusion proteins in which the heavy chain includes cysteines at both positions (a) 239 and (b) 294 or 295 are treated with a reducing agent before conjugation to inhibit formation of disulfide bonds, particularly intramolecular disulfides between cysteines at positions 239 and either 294 or 295. Preferably, the reducing agent is included in a culture medium used for culturing the antibody. Examples of suitable reducing agents for protecting sulfhydryl bonds include dithiothreitol, betamercaptoethanol or tris(2-carboxyethyl)phosphine, or any combination thereof. A preferred reducing agent is dithiothreitol in culture medium. The concentration of dithiothreitol or other reducing agent in culture medium can be e.g., 0.1-5 mM, or 0.5-2.5 or 0.9 to 1.5 mM.

Conversely antibodies or fusion proteins with cysteines at positions 239 and either 294 or 295, when cultured in a medium without a reducing agent develop hypersialyation and/or tri and tetra antennary branching of the GlcNac V. Antibody Drug Conjugates The cysteine residues introduced into a heavy chain constant region provide sites for conjugation to a drug, particularly cytotoxic or cytostatic moieties as antibody drug conjugates (ADCs). In comparison with naked antibodies, ADCs provide additional mechanisms, particularly delivery of a toxic moiety coupled to the antibody to the interior of a cell, thereby killing the cell or otherwise inhibiting its proliferation. Currently four ADCs are marketed: brentuximab vedotin (anti-CD30 trade name: ADCETRIS®, marketed by Seattle Genetics and Millennium/Takeda), trastuzumab emtansine (anti-HER2, trade name: Kadcyla®, marketed by Genentech and Roche) inotuzumab ozogamicin (anti-CD22, trade name Besponsa, marketeed by Pfizer and gemtuzumab ozogamicin (anti-CD33, trade name: Mylotarg, marketed by Pfizer). Many other ADCs are at various stages of development.

Techniques for conjugating drugs to antibodies are well-known (see, e.g., Arnon et al., "Monoclonal Antibodies For Immunotargeting Of Drugs In Cancer Therapy," in *Monoclonal Antibodies And Cancer Therapy* (Reisfeld et al. eds., Alan R. Liss, Inc., 1985); Hellstrom et al., "Antibodies For Drug Delivery," in Controlled Drug Delivery (Robinson et al. eds., Marcel Dekker, Inc., 2nd ed. 1987); Thorpe, "Antibody Carriers Of Cytotoxic Agents In Cancer Therapy: A Review," in *Monoclonal Antibodies '84: Biological And Clinical Applications* (Pinchera et al. eds., 1985); "Analysis, Results, and Future Prospective of the Therapeutic Use of Radiolabeled Antibody In Cancer Therapy," in *Monoclonal Antibodies For Cancer Detection And Therapy* (Baldwin et al. eds., Academic Press, 1985); and Thorpe et al., 1982, *Immunol. Rev.* 62:119-58. See also, e.g. WO 89/12624).

Cysteine contains a free sulfhydryl group, which is more nucleophilic than amines and is generally the most reactive functional group in a protein. Sulfhydryls, unlike most amines, are generally reactive at neutral pH, and therefore can be coupled to other molecules selectively in the presence of amines. This selectivity makes the sulfhydryl group the linker of choice for coupling antibodies. The mean number of molecules drug per molecule antibody is often 1, 2, 3, or 4.

The drug can be conjugated in a manner that reduces its activity unless it is cleaved off the antibody (e.g., by hydrolysis, by antibody degradation or by a cleaving agent). Such a drug is attached to the antibody with a cleavable linker that is sensitive to cleavage in the intracellular environment of a target cell but is not substantially sensitive to the extracellular environment, such that the conjugate is cleaved from the antibody when it is internalized by the target cell (e.g., in the endosomal environment or, for example by virtue of pH sensitivity or protease sensitivity, in the lysosomal environment or in the caveolear environment).

Typically the ADC comprises a linker region between the drug and the antibody. The linker may be cleavable under intracellular conditions, such that cleavage of the linker releases the drug from the antibody in the intracellular environment (e.g., within a lysosome or endosome or caveolea). The linker can be, e.g., a peptidyl linker cleaved by an intracellular peptidase or protease enzyme, including a lysosomal or endosomal protease. Typically, the peptidyl linker is at least two amino acids long or at least three amino acids long. Cleaving agents can include cathepsins B and D and plasmin (see, e.g., Dubowchik and Walker, 1999, *Pharm. Therapeutics* 83:67-123). Most typical are peptidyl linkers that are cleavable by enzymes that are present in target cells. For example, a peptidyl linker that is cleavable by the thiol-dependent protease cathepsin-B, which is highly expressed in cancerous tissue, can be used (e.g., a linker comprising a Phe-Leu or a Gly-Phe-Leu-Gly peptide). Other such linkers are described, e.g., in U.S. Pat. No. 6,214,345. An exemplary peptidyl linker cleavable by an intracellular protease comprises a Val-Cit linker or a Phe-Lys dipeptide (see, e.g., U.S. Pat. No. 6,214,345, which describes the synthesis of doxorubicin with the Val-Cit linker). One advantage of using intracellular protease release of the drug is that the agent is typically attenuated when conjugated and the serum stabilities of the conjugates are typically high.

The cleavable linker can be pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264:14653-14661.) Such linkers are relatively stable under neutral pH conditions, such as those in the blood, but are unstable at below pH 5.5 or 5.0, the approximate pH of the lysosome. One example of such a hydrolyzable linker is a thioether linker (such as, e.g., a thioether attached to the drug via an acylhydrazone bond (see, e.g., U.S. Pat. No. 5,622,929)).

Other linkers are cleavable under reducing conditions (e.g., a disulfide linker). Disulfide linkers include those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene). (See, e.g., Thorpe et al., 1987, *Cancer Res.* 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935).

The linker can also be a malonate linker (Johnson et al., 1995, *Anticancer Res.* 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10):1305-12).

The linker also can be a non-cleavable linker, such as a maleimido-alkylene- or maleimide-aryl linker that is directly attached to a drug. An active drug-linker is released by degradation of the antibody.

The linker is one that comprises a functional group that is reactive to a group present on the antibody. For example, the linker can be linked to the antibody via a disulfide bond between a sulfur atom of the linker and a sulfur atom of the antibody. As another example, the linker can form a bond with a sulfur atom of the antibody via a maleimide group of a stretcher unit. The sulfur atom can be from a cysteine residue of an interchain disulfide or from a cysteine residue introduced into the antibody.

Useful classes of cytotoxic agents to conjugate to antibodies include, for example, antitubulin agents, DNA minor groove binding agents, DNA replication inhibitors, chemotherapy sensitizers, a pyrrolobenzodiazepine dimer or the like. Other exemplary classes of cytotoxic agents include anthracyclines, auristatins, camptothecins, duocarmycins, etoposides, maytansinoids and vinca alkaloids. Some exemplary cytotoxic agents include auristatins (e.g., auristatin E, AFP, MMAF, MMAE), DNA minor groove binders (e.g., enediynes and lexitropsins), duocarmycins, taxanes (e.g., paclitaxel and docetaxel), vinca alkaloids, doxorubicin, morpholino-doxorubicin, and cyanomorpholino-doxorubicin.

The cytotoxic agent can be a chemotherapeutic such as, for example, doxorubicin, paclitaxel, melphalan, *vinca* alkaloids, methotrexate, mitomycin C or etoposide. The agent can also be a CC-1065 analogue, calicheamicin, maytansine, an analog of dolastatin 10, rhizoxin, or palytoxin.

The cytotoxic agent can also be an auristatin. The auristatin can be an auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatins include auristatin phenylalanine phenylenediamine (AFP), monomethyl auristatin F (MMAF), and monomethyl auristatin E (MMAE). The synthesis and structure of various auristatins are described in, for example, US 2005-0238649 and US2006-0074008.

The cytotoxic agent can be a DNA minor groove binding agent. (See, e.g., U.S. Pat. No. 6,130,237.) For example, the minor groove binding agent can be a CBI compound or an enediyne (e.g., calicheamicin). Another class of minor groove binding agents are pyrrolobenzodiazepine (PBD) dimers. PBDs exert their biological activity through covalent binding via their N10-C11 imine/carbinolamine moieties to the C2-amino position of a guanine residue within the minor groove of DNA. Exemplary antibody-drug conjugates include PBD based antibody-drug conjugates; i.e., antibody-drug conjugates wherein the drug component is a PBD drug.

PBDs are of the general structure:

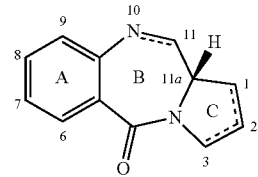

They differ in the number, type and position of substituents, in both their aromatic A rings and pyrrolo C rings, and in the degree of saturation of the C ring. In the B-ring there is either an imine (N═C), a carbinolamine (NH—CH(OH)), or a carbinolamine methyl ether (NH—CH(OMe)) at the N10-C11 position, which is the electrophilic center responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site. The ability of PBDs to form an adduct in the minor groove enables them to interfere with DNA processing, hence their use as antitumor agents.

The biological activity of these molecules can be potentiated by joining two PBD units together through their C8/C'-hydroxyl functionalities via a flexible alkylene linker. The PBD dimers are thought to form sequence-selective DNA lesions such as the palindromic 5'-Pu-GATC-Py-3' interstrand cross-link, which is thought to be mainly responsible for their biological activity.

In some embodiments, PBD based antibody-drug conjugates comprise a PBD dimer linked to an antibody. The monomers that form the PBD dimer can be the same or different, i.e., symmetrical or unsymmetrical. The PBD dimer can be linked to the antibody at any position suitable for conjugation to a linker. For example, in some embodiments, the PBD dimer will have a substituent at the C2 position that provides an anchor for linking the compound to the antibody. In alternative embodiments, the N10 position of the PBD dimer will provide the anchor for linking the compound to the antibody.

Typically the PBD based antibody-drug conjugate comprises a linker between the PBD drug and the antibody binding to the antigen of the primary cancer. The linker may comprise a cleavable unit (e.g., an amino acid or a contiguous sequence of amino acids that is a target substrate for an enzyme) or a non-cleavable linker (e.g., linker released by degradation of the antibody). The linker may further comprise a maleimide group for linkage to the antibody, e.g., maleimidocaproyl. The linker may, in some embodiments, further comprise a self-immolative group, such as, for example, a p-aminobenzyl alcohol (PAB) unit.

An exemplary PBD for use as a conjugate is described in International Application No. WO 2011/130613 and is as follows wherein the wavy line indicates the site of attachment to the linker:

or a pharmaceutically acceptable salt thereof. An exemplary linker is as follows wherein the wavy line indicates the site of attachment to the drug and the antibody is linked via the maleimide group.

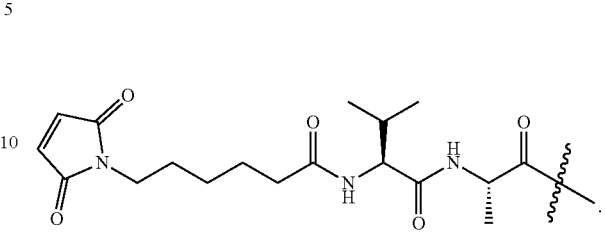

Exemplary PBDs based antibody-drug conjugates include antibody-drug conjugates as shown below wherein Ab is an antibody as described herein:

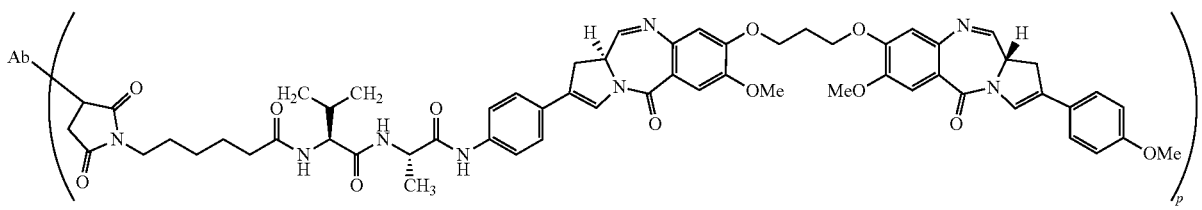

or a pharmaceutically acceptable salt thereof. The drug loading is represented by p, the number of drug-linker molecules per antibody.

The cytotoxic or cytostatic agent can be an anti-tubulin agent. Examples of anti-tubulin agents include taxanes (e.g., Taxol® (paclitaxel), Taxotere® (docetaxel)), T67 (Tularik), vinca alkyloids (e.g., vincristine, vinblastine, vindesine, and vinorelbine), and auristatins (e.g., auristatin E, AFP, MMAF, MMAE, AEB, AEVB). Exemplary auristatins are shown below in formulae III-XIII. Other suitable antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

The cytotoxic agent can be a maytansinoid, another group of anti-tubulin agents. For example, the maytansinoid can be maytansine or a maytansine containing drug linker such as DM-1 or DM-4 (ImmunoGen, Inc.; see also Chari et al., 1992, Cancer Res. 52:127-131).

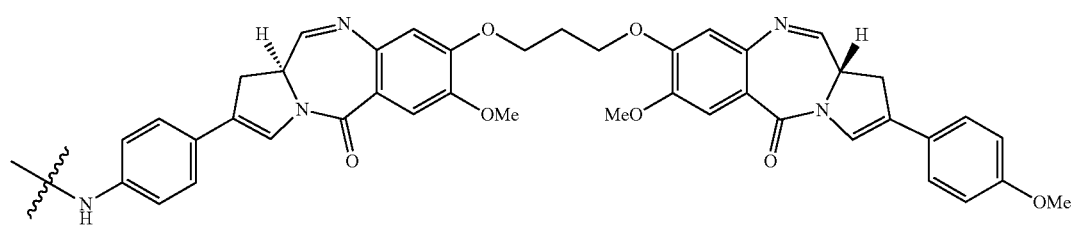 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

Exemplary antibody drug conjugates include vcMMAE and mcMMAF antibody drug conjugates as follows wherein p represents the drug loading and typically ranges from 1 to 4, preferably 2 or 4 and Ab is an antibody:

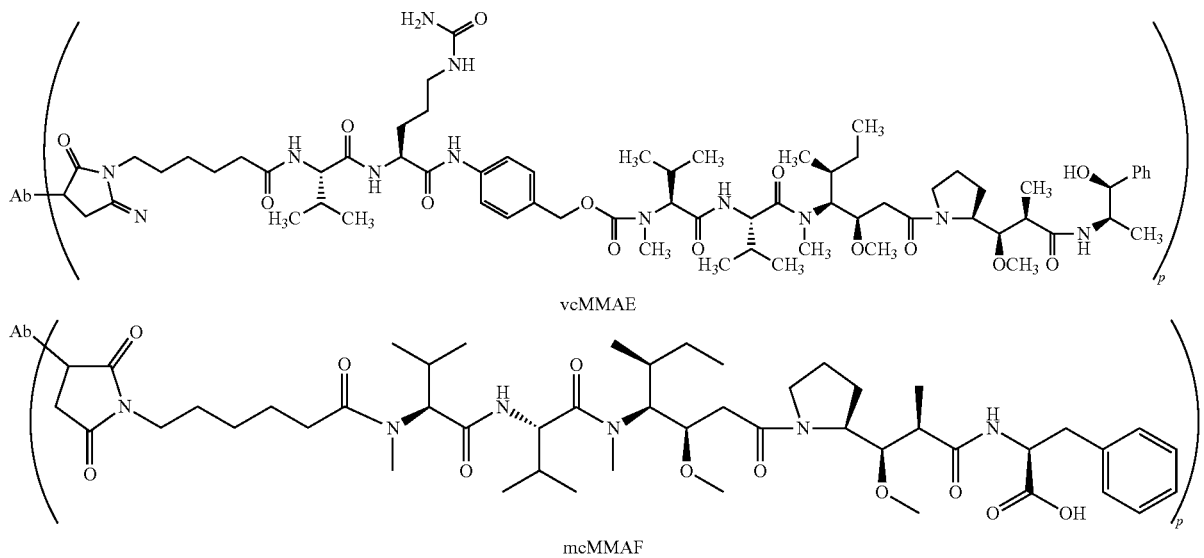

vcMMAE mcMMAF

Other cytotoxic agents for conjugation to an antibody are tubulysins and analogs thereof, which is another group of anti-tubulin agents as exemplified below.

In some aspects, those cytotoxic agents are conjugated to an antibody via a beta-glucuronidelinker. The glucuronide linker is a hydrophilic alternative to protease cleavable linkers, such as valine-citruline and valine alanine and exploits intracellular beta glucuronidase to initiate drug release.

The position 295 or 294 and 239 dual cysteine variants are particularly suitable for conjugation to hydrophobic drugs because the site of conjugation proximate to glycan residues serves to mask the hydrophobic drug. Tubulysins and glucuronide linkers attached to these cytotoxic agents are more fully described in WO2016040684.

Non-limiting examples of glucuronide-linked tubulysin Drug Linker compounds for conjugation to the dual cysteine residues are given by compounds 8 and 9 (below) in which the tubulysin Drug unit is tubulysin M or desmethyl tubulysin M. Tubulysin M is also known as:

(αS,γR)-γ-[[[2-[(1R,3R)-1-(Acetyloxy)-4-methyl-3-[methyl[(2S,3S)-3-methyl-2-[[[(2R)-1-methyl-2-piperidinyl]carbonyl]amino]-1-oxopentyl]amino]pentyl]-4-thiazolyl]carbonyl]amino]-α-methyl-Benzenepentanoic Acid and has CAS Number 936691-46-2.

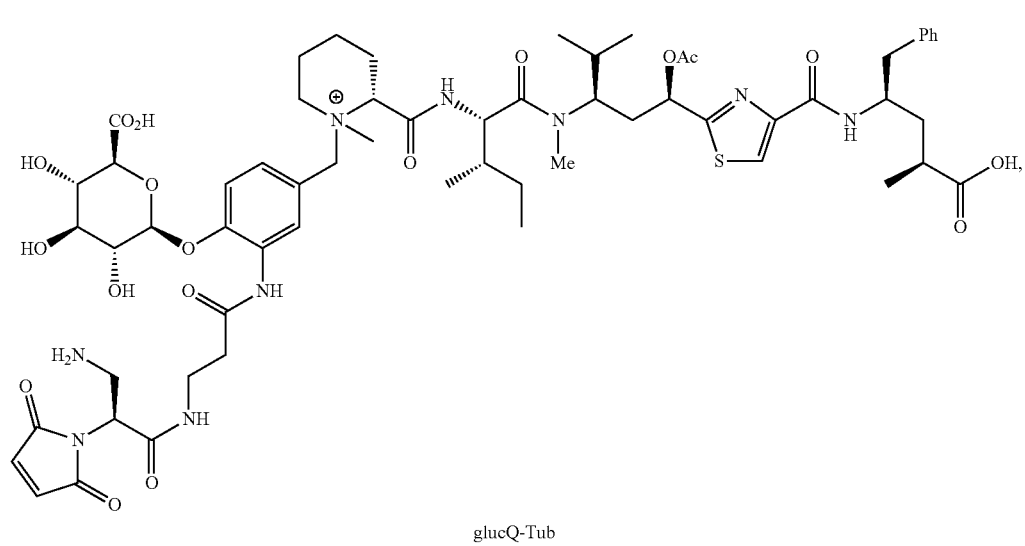

glucQ-Tub

8

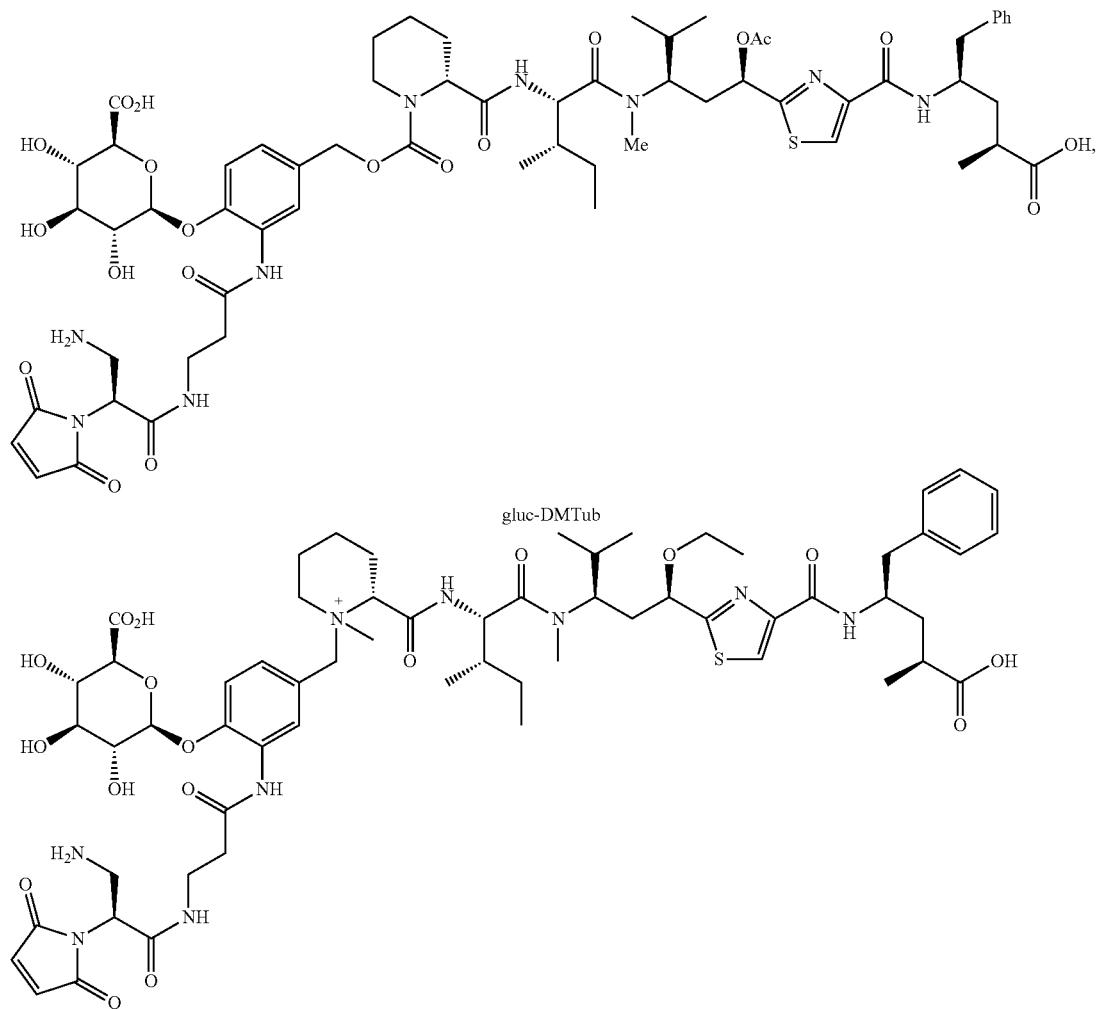
An ether variant of tubulysin M linked to a glucuronide linker is shown above.
Preparation of the glucuronide-based tubulysin drug linker compound 8 and tubulysin ester and ether variants thereof detailed in WO20160404684, and specifically incorporated by reference herein, are exemplified by the following reaction schemes:
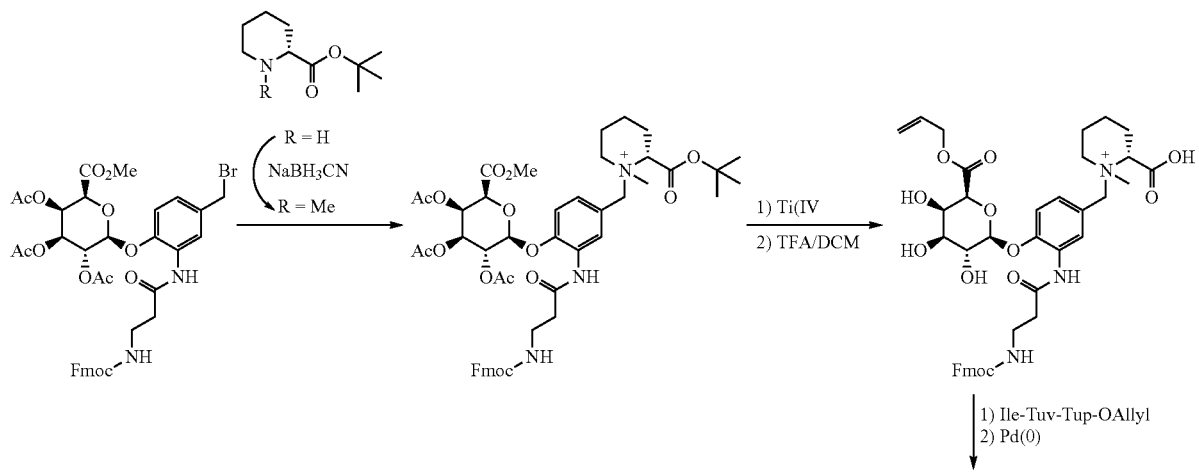

-continued

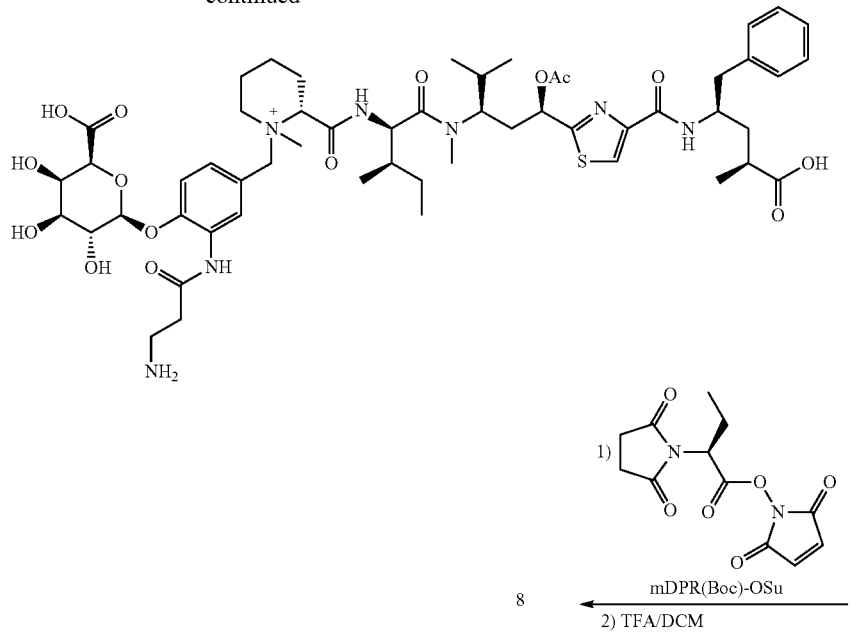

Preparation of mDPR(Boc)-OH, which is converted to its activated esters mDPR(BOC)-OSu and mDPR(BOC)-OPFF, is described in Nature Biotech, 2014, 32, 1059-1062), the procedure for which is specifically incorporated by reference herein, and preparation of the glucuronide intermediate, which is brominated for quaternization of tubulysin M, is described by Molecular Cancer Therapeutics 15, 938-945 (2016), the procedure for which is specifically incorporated by reference herein.

Antibody drug conjugates of tubulysin M and analogs thereof in which the acetate group of the tubuvaline reside is replaced by an ether or another ester group that have attachment of a glucuronide linker to the tertiary amine nitrogen of the tubulysin Mep residue through quaternization of that nitrogen atom, and which may be prepared from Drug Linker compounds such as those described above, are exemplified as follows:

prop-1-yl, or vinyl, or R2A is methyl, ethyl, propyl, iso-propyl, prop-2-en-1-yl or 2-methyl-prop-2-en-1-yl and wherein R7B is —H or —OH, wherein p represents the drug loading and typically ranges from 1 to 4, and in some aspects is 2 or 4, Ab is an antibody and S is a sulfur atom from cysteine 295 or cysteine 239.

Antibodies or fusion proteins can also be conjugated via cysteine occupying position 295 and optionally 239 to detectable markers such as an enzyme, a chromophore, or a fluorescent label.

As well as being conjugated to a drug or label antibodies can also be linked via a cleavable linker attached to an inhibitory or masking domain that inhibits antibody binding (see, e.g., WO2003/068934, WO2004/009638, WO 2009/025846, WO2101/081173 and WO2014103973). The linker can be designed to be cleaved by enzymes that are specific to certain tissues or pathologies, thus enabling the antibody to be preferentially activated in desired locations. Masking

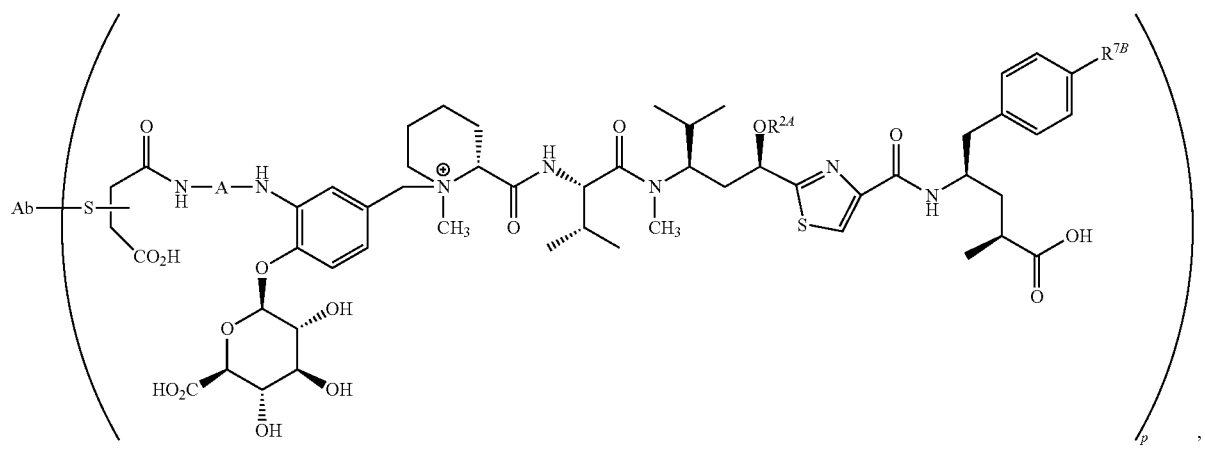

wherein R2A is —C(═O)R2B, wherein R2B is methyl, ethyl, propyl, iso-propyl, 3-methyl-prop-1-yl, 3,3-dimethylmoieties can act by binding directly to the binding site of an antibody or can act indirectly via steric hindrance.

VI. Targets

Some such antibodies are immunospecific for a cancer cell antigen, preferably one on the cell surface internalizable within a cell on antibody binding. Targets to which antibodies can be directed include receptors on cancer cells and their ligands or counter-receptors (e.g., CD3, CD19, CD20, CD22, CD30, CD33, CD34, CD40, CD44, CD47, CD52, CD70, CD79a, CD123, Her-2, EphA2, GPC3 lymphocyte associated antigen 1, VEGF or VEGFR, CTLA-4, LIV-1, nectin-4, CD74, and SLTRK-6).

Some examples of commercial antibodies and their targets suitable for application of the present methods include brentuximab or brentuximab vedotin, CD30, alemtuzumab, CD52, rituximab, CD20, trastuzumab Her/neu, nimotuzumab, cetuximab, EGFR, bevacizumab, VEGF, palivizumab, RSV, abciximab, GpIIb/IIIa, infliximab, adalimumab, certolizumab, golimumab TNF-alpha, baciliximab, daclizumab, IL-2, omalizumab, IgE, gemtuzumab or vadastuximab, CD33, natalizumab, VLA-4, vedolizumab alpha4beta7, belimumab, BAFF, otelixizumab, teplizumab CD3, ofatumumab, ocrelizumab CD20, epratuzumab CD22, alemtuzumumab CD52, eculizumab C5, canakimumab IL-1beta, mepolizumab IL-5, reslizumab, tocilizumab IL-6R, ustekinumab, briakinumab IL-12, 23, hBU12 (CD19) (US20120294853), humanized 1F6 or 2F12 (CD70) (US20120294863), BR2-14a and BR2-22a (LIV-1) (WO2012078688). Some sequences of exemplary antibodies are provided in the sequence listing.

VII. Pharmaceutical Compositions and Methods of Treatment

Antibody drug conjugates produced in accordance with the methods described above are administered in an effective regime meaning a dosage, route of administration and frequency of administration that delays the onset, reduces the severity, inhibits further deterioration, and/or ameliorates at least one sign or symptom of the disease it is intended to treat, such as cancer, autoimmune disease or infection including any of the indications discussed above. If a patient is already suffering from the disease, the regime can be referred to as a therapeutically effective regime. If the patient is at elevated risk of the disease relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for antibody drug conjugates are 0.001 mg/kg to 100 mg/kg, 5 mg-50 mg/kg, 10 mg-25 mg/kg, 1 mg/kg to 7.5 mg/kg, or 2 mg/kg to 7.5 mg/kg or 3 mg/kg to 7.5 mg/kg of the subject's body weight, or 0.1-20, or 0.5-5 mg/kg body weight (e.g., 0.5, 1, 2, 3, 4, 5, 6, 7, 8, 9 or 10 mg/kg) or 10-15000, 200-15000 or 500-10,000 mg as a fixed dosage. Exemplary dosages for active monoclonal antibody drug conjugates thereof, e.g., conjugated to auristatins or tubulysins, are 1 mg/kg to 7.5 mg/kg, or 2 mg/kg to 7.5 mg/kg or 3 mg/kg to 7.5 mg/kg of the subject's body weight, or 0.1-20, or 0.5-5 mg/kg body weight (e.g., 0.5, 1, 2, 3, 4, 5, 6, 7, 8, 9 or 10 mg/kg) or 10-1500 or 200-1500 mg as a fixed dosage. Exemplary dosages for highly active monoclonal antibody drug conjugates thereof, e.g., conjugated to PBDs, are 1.0 µg/kg to 1.0 mg/kg, or 1.0 µg/kg to 500.0 µg/kg of the subject's body weight.

In some methods, the patient is administered the ADC every two, three or four weeks. The dosage depends on the frequency of administration, condition of the patient and response to prior treatment, if any, whether the treatment is prophylactic or therapeutic and whether the disorder is acute or chronic, among other factors. The dose also depends on the decrease in binding, effector function or cytotoxicity.

Administration can be parenteral, intravenous, oral, subcutaneous, intra-arterial, intracranial, intrathecal, intraperitoneal, topical, intranasal or intramuscular. Administration can also be localized directly, such as into a tumor. Administration into the systemic circulation by intravenous or subcutaneous administration is preferred. Intravenous administration can be, for example, by infusion over a period such as 30-90 min or by a single bolus injection.

The frequency of administration depends on the half-life of the antibody in the circulation, the condition of the patient and the route of administration among other factors. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are between weekly or three out of every four weeks over a continuous course of treatment, although more or less frequent dosing is also possible. For subcutaneous administration, an exemplary dosing frequency is daily to monthly, although more or less frequent dosing is also possible.

The number of dosages administered depends on the nature of the disease (e.g., whether presenting acute or chronic symptoms) and the response of the disorder to the treatment. For acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic (240-360 mOsm/kg) and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of antibody in a liquid formulation can be e.g., 1-100 mg/ml, such as 10 mg/ml.

Treatment with antibodies of the invention can be combined with chemotherapy, radiation, stem cell treatment, surgery, anti-virals, antibiotics, immune suppressants or stimulants, or other treatments effective against the disorder being treated. Useful classes of other agents that can be administered with ADC's for treatment of cancers or autoimmune disease include, for example, antibodies to other receptors expressed on cancerous cells, antitubulin agents (e.g., auristatins), DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Treatment with the antibodies can increase the median progression-free survival or overall survival time of patients with tumors, especially when relapsed or refractory, by at least 30% or 40% but preferably 50%, 60% to 70% or even 100% or longer, compared to the same treatment (e.g., chemotherapy) but without an antibody. In addition or alternatively, treatment (e.g., standard chemotherapy) including the antibody can increase the complete response rate, partial response rate, or objective response rate (complete+partial) of patients with tumors by at least 30% or 40% but preferably 50%, 60% to 70% or even 100% compared to the same treatment (e.g., chemotherapy) but without the antibody.

Typically, in a clinical trial (e.g., a phase II, phase II/III or phase III trial), the aforementioned increases in median progression-free survival and/or response rate of the patients treated with standard therapy plus the antibody, relative to the control group of patients receiving standard therapy alone (or plus placebo), are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration.

Although the invention has been described in detail for purposes of clarity of understanding, certain modifications may be practiced within the scope of the appended claims. All publications, accession numbers, web sites, patent documents and the like cited in this application are hereby incorporated by reference in their entirety for all purposes to the same extent as if each were so individually denoted. To the extent different information is associated with a citation at different times, the information present as of the effective filing date of this application is meant. The effective filing date is the date of the earliest priority application disclosing the accession number in question. Unless otherwise apparent from the context any element, embodiment, step, feature or aspect of the invention can be performed in combination with any other.

Examples

Antibody Expression and Purification

DNA strings containing the IgG1 Fc mutations were cloned into expression vectors using Gibson Assembly. Cysteine mutant plasmids along with corresponding light chain were transfected into Freestyle CHO-S cells and the resultant supernatants were harvested after 9 days. The antibodies containing the cysteine mutations in the heavy chain were purified by Mab select protein A affinity columns.

Glycan Analysis

Cysteine engineered antibodies were assessed for mass and glycan content using reversed phase (RP) UPLC-MS. Antibodies were reduced using DTT and then analyzed with and without deglycosylated treatment (PNGase).

Maleimide and Tubulysin Stability Assays

To assess maleimide hydrolysis and stability, the cysteine engineered antibodies were conjugated using vcMMAE and then incubated in rat plasma for 0, 4 and 7 days. ADCs were purified from plasma using anti-human capture resin, reduced with DTT and then analyzed using RP UPLC-MS. Maleimide hydrolysis was identified by analyzing heavy chain containing drug and assessing a mass addition of 18 Daltons. Maleimide stability was assessed by comparing the DAR (drug antibody ratio) at each time point. Drug loss was measured as a loss of 1317 Daltons and calculated as a percentage of total drug remaining based on total drug at t=0.

To assess tubulysin stability, the cysteine mutated antibodies were conjugated using tubulysin M and then incubated in rat plasma for 0, 4 and 7 days. ADCs were purified from plasma using anti-human capture resin, reduced and then analyzed using RP UPLC-MS. Tubulysin acetate hydrolysis was identified by analyzing heavy chain containing drug and assessing a mass loss of 42 Daltons.

Cell Culture

Hep3B, HepG2, and Huh7 cells were obtained from ATCC. JHH-7 cells were obtained from Creative Bioarray respectively. Hep3B and HepG2 cells were grown in EMEM containing 10% FBS in a 37° C. humidified incubator with 5% CO2. Huh7 cells were grown in DMEM containing 10% FBS in a 37° C. humidified incubator with 5% CO2. JHH-7 cells were grown in Williams-E containing 10% FBS in a 37° C. humidified incubator with 5% CO2.

In Vitro Cytotoxicity

Assays were performed in 384-well tissue culture treated plates and cell viability was assessed using CellTiter Glo® (Promega). 1250 Hep3B, HepG2, or Huh7, or 1500 JHH-7 cells/well were plated in 40 µL of the appropriate media. 24 hours after plating, cells were treated 104 with the indicated test articles at the appropriate concentrations. 96 hours after dosing, 104 of CellTiter Glo was added to each well and total luminescence was measure with an Envision multi-label plate reader (PerkinElmer). Average percent viabilities and standard deviations were calculated from quadruplicates relative to control vehicle treated cells.

In Vivo Antitumor Activity

Animal studies were conducted following Institutional Animal Care and Use Committee protocols. $2.5 \times 10^6$ Hep3B or $5 \times 10^5$ JHH-7 cells were implanted subcutaneously in athymic nude mice. Tumor growth was monitored throughout the course of the study with bilateral vernier caliper measurements, and mean tumor volumes were calculated using the equation ($0.5 \times [\text{length} \times \text{width}^2]$). When tumors reached approximately 100 mm$^3$, mice were randomly assigned to the indicated treatment groups and dosed intraperitoneally with a single 200 µL dose of appropriate treatment. For the Hep3B study, each treatment group consisted of 5 mice. For the JHH-7 study, each treatment group consisted of 6 mice. Tumors were measured two times per week and animals were sacrificed when tumors reached 1000 mm$^3$.

Figure 1:
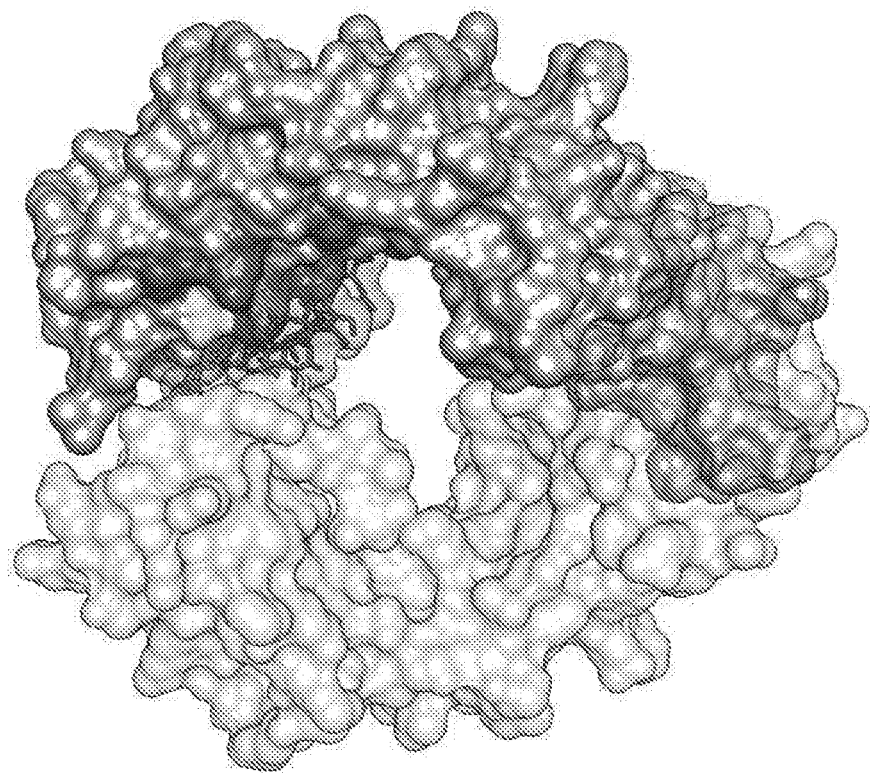
FIG. 1 shows a model of antibody structure illustrating the relative positions of sites of mutation and glycan chains.
Figure 1:
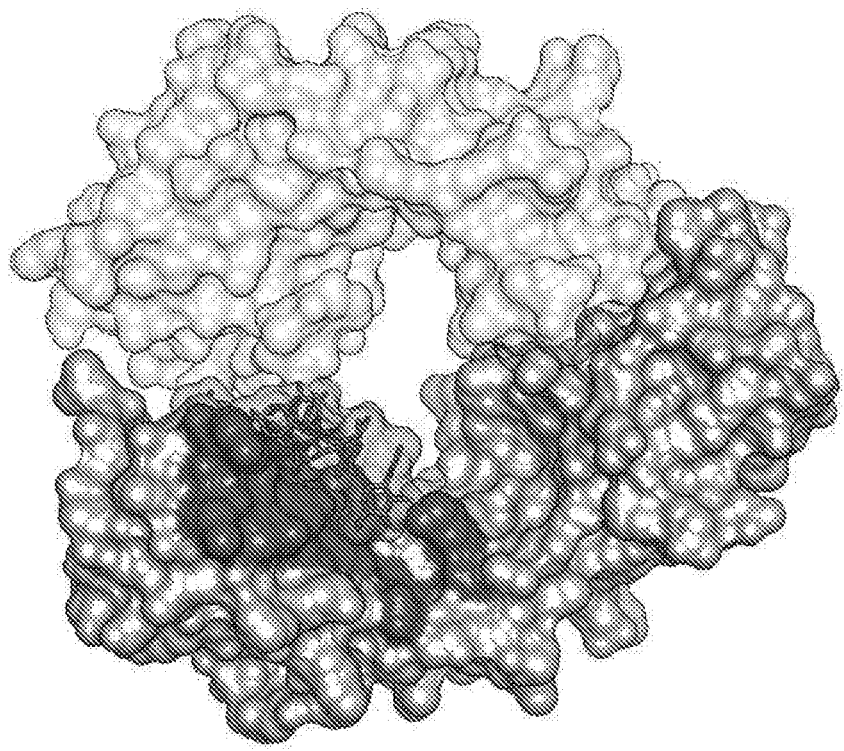

Results 20 mutations were selected as potential sites for conjugation based on the physical proximity to glycan chains at position 297, as shown in FIG. 1. It was thought the glycan chains may serve to mask a hydrophobic drug linked to the conjugation site. 14 mutations were successfully expressed and conjugated. 8 mutations were selected to be combined with S239C as double mutants. Double mutations were expressed and conjugated.

Figure 2:
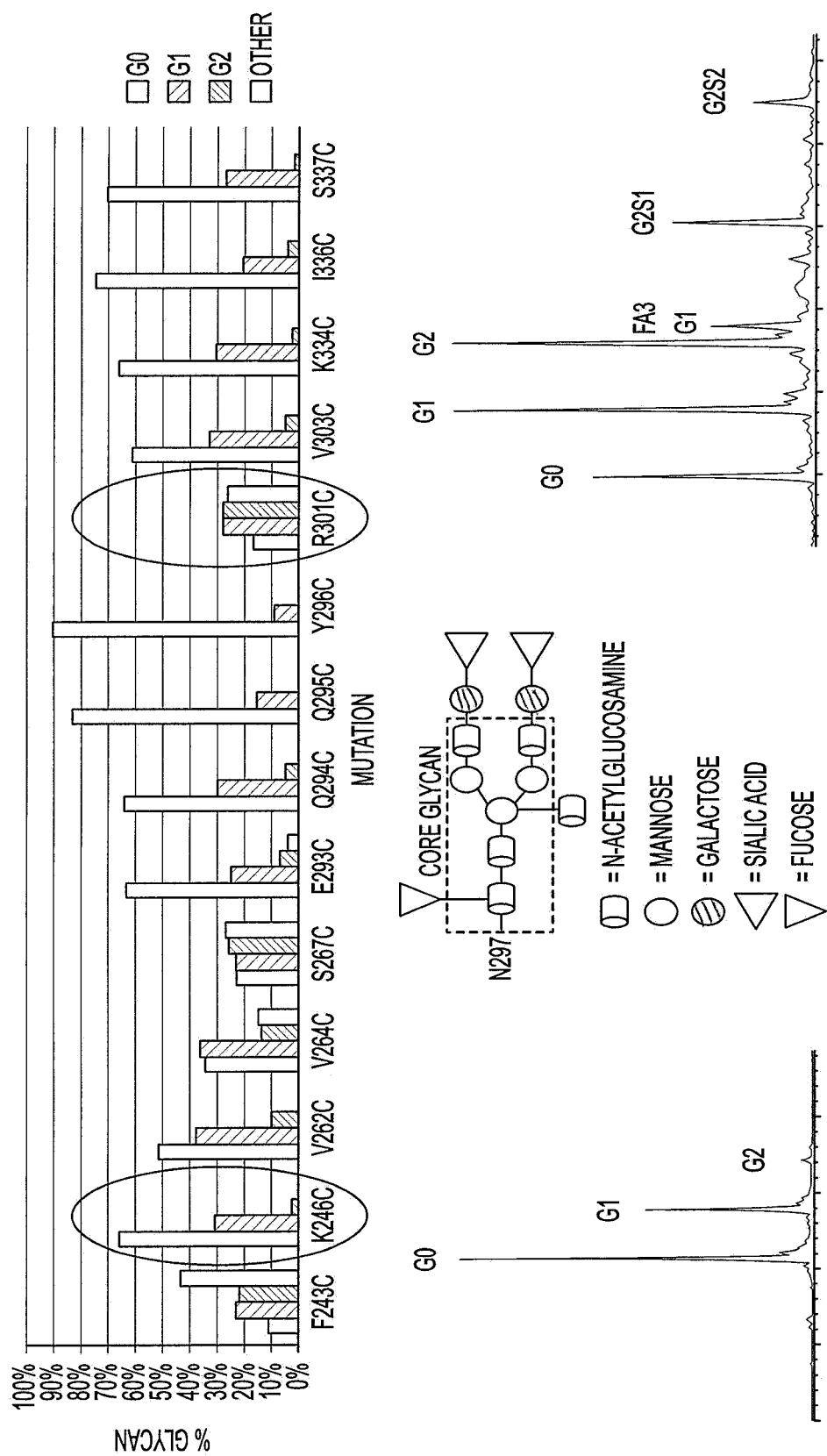
FIG. 2 shows that introduction of mutations resulted in an altered glycan distribution.

FIG. 2 shows the distribution of glycans for different mutations. A glycan distribution of mainly G0, with smaller amounts of G1, G2 and other is preferred. The glycan distribution of Q295C is thus advantageous (as is K246C, E294C, Y296C, V303C, K334C, I336C and S337C), whereas R301C, F243C, V262C, V264C, S267C are not.

Antibodies conjugated to tubulysin were soaked in rat plasma for 7 days at 37° C. ADCs were then purified and assessed for drug degradations using mass spectrometry. A crude plasma mixture was assessed using an in vitro cytotoxicity assay for loss in potency.

Figure 3:
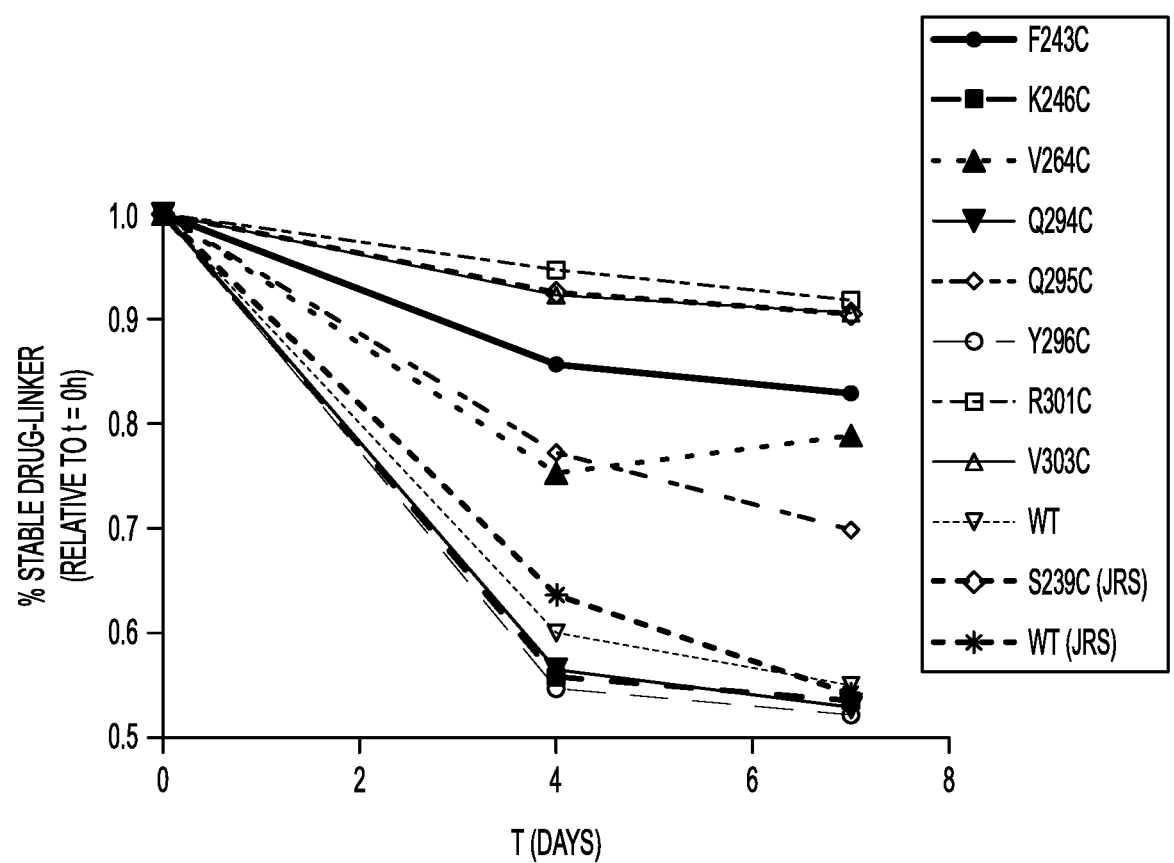
FIG. 3 shows maleimide stability after subjecting vcM-MAE ADCs to rat plasma for seven days.

FIG. 3 shows that Q295C showed intermediate stability of a maleimide linker. S239C showed the greatest maleimide stability of the mutations tested.

Figure 4:
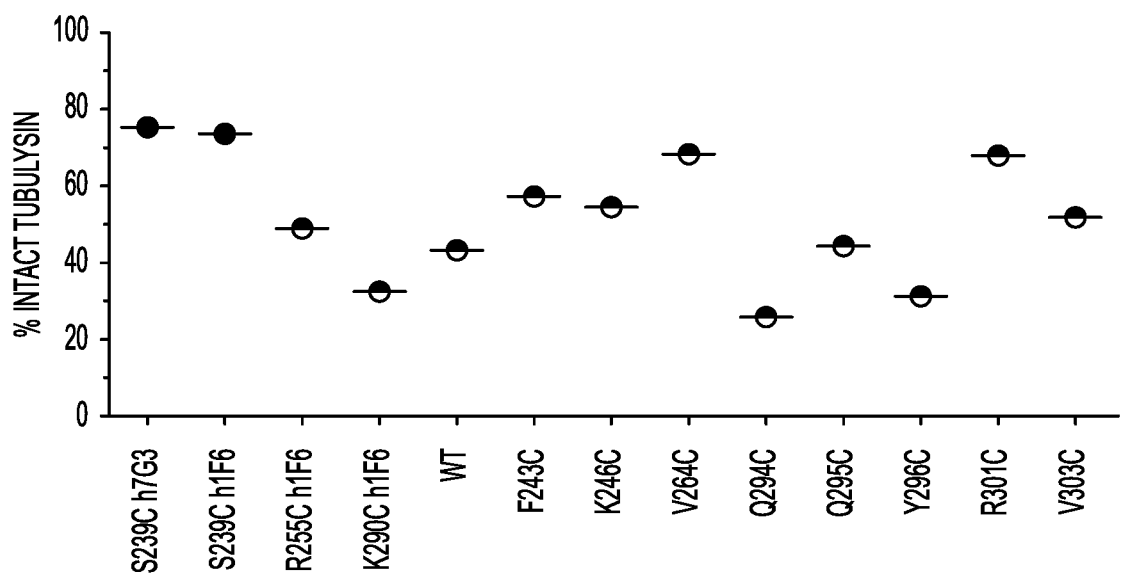
FIG. 4 shows tubulysin stability after subjecting tubulysin ADCs to rat plasma for seven days.

FIG. 4 shows that Q295C also showed intermediate stability of the tubulysin drug. Again S239C showed the greatest stability of the mutations tested.

Figure 5:
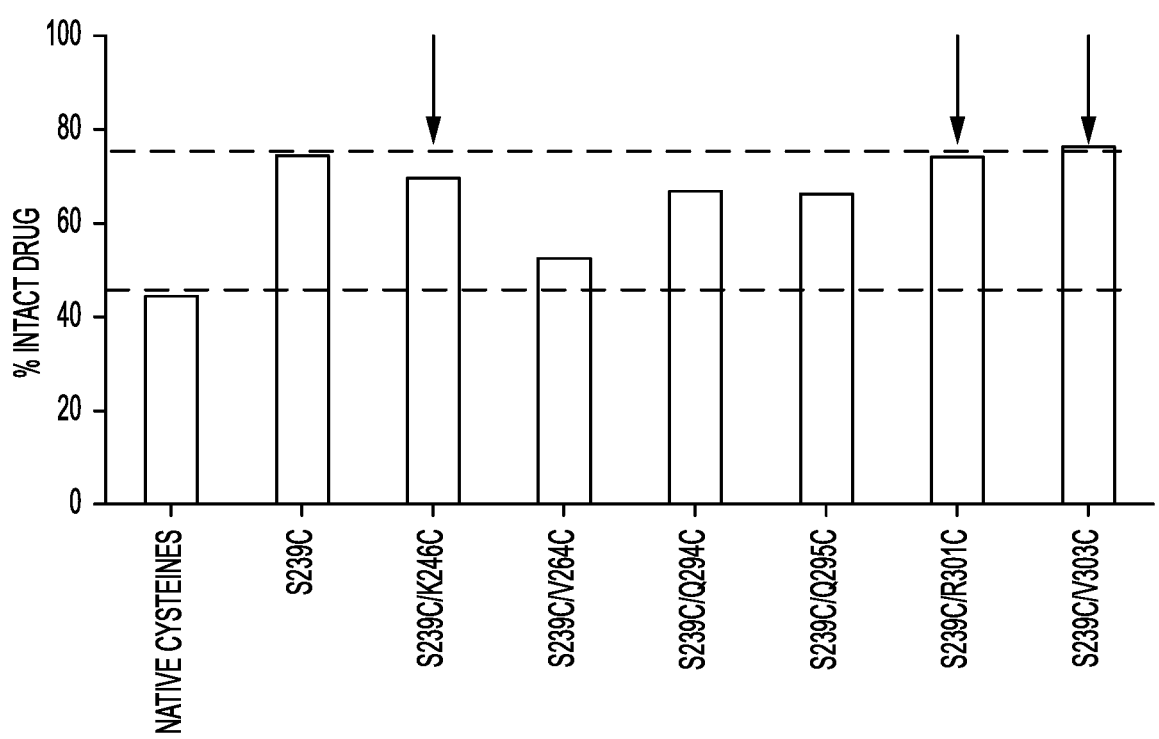
FIG. 5 shows tubulysin stability after subjecting tubulysin ADCs conjugated at two mutant sites after exposure to rat plasma for seven days.

FIG. 5 shows the tubulysin stability of several double mutation combinations in which one mutation is S239C. Q295C showed intermediate stability compared with other mutations tested. However, the stability of the S239C Q295C double mutation was greater than expected from that of the individual mutations represented by the bar in FIG. 6.

FIG. 7 shows the cytotoxicity of various double mutation combinations single against two cancer cell lines. The S239C Q295C double mutant showed intermediate cytotoxicity.

The cytotoxicity of the S239C, Q295C double mutation was compared in a mouse xenograft model with various other conjugates of the same antibody as follows:

4830(8) [AT] 1 mg/kg
5937(4) 2 mg/kg
S239C K246C-5937(4) 2 mg/kg
S239C K290C-5937(4) 2 mg/kg
S239C Q295C-5937(4) 2 mg/kg
S239C V303C-5937(4) 2 mg/kg
S239C K246C V303C-5937(6) 1.33 mg/kg
S239C K246C V303C-6242(6) 1.33 mg/kg
S239C K246C V303C-6238(6) 1.33 mg/kg
S239C K246C V303C Q295C-5937(8) 1 mg/kg
1-6183(8) 1 mg/kg

The doses shown deliver equal moles of drug regardless of the stoichiometry of drug loading.

FIG. 8 shows that the S239C Q295C double mutant conjugated to tubulysin showed the greatest inhibition of tumor growth on the tumor Hep3B-8. FIG. 9 shows the same conclusion for the JHH7-E tumor cell line.

Glycan Analysis of Double Mutations

Antibodies containing the single point mutations S239C or Q295C contain canonical glycosylation patterns (FIGS. 10A-D). Pairing mutations S239C and Q295C results in abnormalities with the N-linked glycan. These abnormal glycans (Table 1) include hypersialyation, as well as tri and tetra antennary branching of the GlcNac. It was shown that these glycosylation patterns are conserved using both transient (FIG. 10D) and stable (FIG. 11) CHO cell production techniques. In addition, paring S239C with E294C also demonstrates this similar glycosylation pattern (FIG. 12).

Analysis of these molecules by non-reduced RP-MS and non-reduced peptide mapping (FIG. 13) demonstrate intrachain disulfide stapling of the engineered cysteine sites in close proximity to the N-linked glycan. Conventional reduction and reoxidation of these antibodies removes this stapling and leaves the engineered sites available for conjugation with the abnormal glycan remaining.

Cell Culture Using DTT (Dithiothreitol)

Antibodies containing the dual mutation S239C and Q295C were expressed transiently under reducing conditions. DTT, TCEP and beta-mercaptoethanol (BME) were used as reducing agents at a total concentration of 0.1, 1.0 and 1.2 mM in the cell media (FIG. 14). Analysis of the glycan patterns of these proteins exhibit reduction of glycan complexity when using DTT as part of the media (FIG. 15). Increasing concentrations of DTT correlate to reduction in sialylation as well as tri and tetra antennary branching of the glycan. Antibodies expressed in these reducing conditions appear monomeric by SEC and have similar binding to the parent antibodies. Reduction and oxidation of these antibodies leaves the engineered sites available for conjugation as with the parent antibody.

The glycosylation pattern of S239C/Q295C antibodies was not affected by the cellular expression system. Glycosylation patterns were essentially equivalent when antibodies were expressed in stable-transfected cell lines vs transiently transfected cell line. See, e.g., Table 1 below.

TABLE 1

Glycosylation analysis of transient verses stable expression of S239C/Q295C mutant

| Name | Stable S239C/Q295C | Transient S239C/Q295C | Δ (Transient-Stable) |
|---|---|---|---|
| FA1 | 1.18 | 2.26 | 1.08 |
| A2 | 0.36 | 0.27 | −0.09 |
| FA2 | 17.48 | 22.41 | 4.93 |
| M5 | 2.63 | 2.73 | 0.1 |
| FA1G1 | 0.38 | 0.46 | 0.08 |
| FA2G1a | 4.84 | 5.52 | 0.68 |
| FA2G1b | 3.42 | 5.2 | 1.78 |
| FA2G2 | 10.7 | 12.97 | 2.27 |
| FA2G2S1a | 9.61 | 8.87 | −0.74 |
| FA2G2S1b | 8.24 | 7.46 | −0.78 |
| FA2G2S2 | 15.48 | 10.19 | −5.29 |
| FA3G3S1 | 2.46 | 2.2 | −0.26 |
| FA3G3S2a | 1.39 | 0.85 | −0.54 |
| FA3G3S2b | 0.63 | 0.39 | −0.24 |
| FA3G3S2c | 1.86 | 1.09 | −0.77 |
| FA3G3S3 | 2.37 | 1.1 | −1.27 |
| Bi-antennarity | 70.13 | 72.89 | 2.76 |
| Tri-antennarity | 8.71 | 5.63 | −3.08 |
| Galactosylation | 43.53 | 45.01 | 1.48 |
| Sialylation | 42.04 | 32.15 | −9.89 |
| Unknown | 16.99 | 16.04 | −0.95 |

Sequence Listing

IgG1

(SEQ ID NO: 1)

ASTKGPSVFPLAPSSKSTSGGTAALGCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKCKVSNKALPAPIEKTIS

```
KAKGQPREPQVYTLPPSRDELTKNQVSLTCLVKGFYPSDIAVEWESNGQPENNYKTTPPVLDSDGSFFLYSKL

TVDKSRWQQGNVFSCSVMHEALHNHYTQKSLSLSPGK

IgG2                                                                (SEQ ID NO: 2)
ASTKGPSVFP LAPCSRSTSE STAALGCLVK DYFPEPVTVS WNSGALTSGV

HTFPAVLQSS GLYSLSSVVT VPSSNFGTQT YTCNVDHKPS NTKVDKTVER

KCCVECPPCP APPVAGPSVF LFPPKPKDTL MISRTPEVTC VVVDVSHEDP

EVQFNWYVDG VEVHNAKTKP REEQFNSTFR VVSVLTVVHQ DWLNGKEYKC

KVSNKGLPAP IEKTISKTKG QPREPQVYTL PPSREEMTKN QVSLTCLVKG

FYPSDISVEW ESNGQPENNY KTTPPMLDSD GSFFLYSKLT VDKSRWQQGN

VFSCSVMHEA LHNHYTQKSL SLSPGK

IgG3                                                                (SEQ ID NO: 3)
ASTKGPSVFP LAPCSRSTSG GTAALGCLVK DYFPEPVTVS WNSGALTSGV

HTFPAVLQSS GLYSLSSVVT VPSSSLGTQT YTCNVNHKPS NTKVDKRVEL

KTPLGDTTHT CPRCPEPKSC DTPPPCPRCP EPKSCDTPPP CPRCPEPKSC

DTPPPCPRCP APELLGGPSV FLFPPKPKDT LMISRTPEVT CVVVDVSHED

PEVQFKWYVD GVEVHNAKTK PREEQYNSTF RVVSVLTVLH QDWLNGKEYK

CKVSNKALPA PIEKTISKTK GQPREPQVYT LPPSREEMTK NQVSLTCLVK

GFYPSDIAVE WESSGQPENN YNTTPPMLDS DGSFFLYSKL TVDKSRWQQG

NIFSCSVMHE ALHNRFTQKS LSLSPGK

IgG4                                                                (SEQ ID NO: 4)
ASTKGPSVFP LAPCSRSTSE STAALGCLVK DYFPEPVTVS WNSGALTSGV

HTFPAVLQSS GLYSLSSVVT VPSSSLGTKT YTCNVDHKPS NTKVDKRVES

KYGPPCPSCP APEFLGGPSV FLFPPKPKDT LMISRTPEVT CVVVDVSQED

PEVQFNWYVD GVEVHNAKTK PREEQFNSTY RVVSVLTVLH QDWLNGKEYK

CKVSNKGLPS SIEKTISKAK GQPREPQVYT LPPSQEEMTK NQVSLTCLVK

GFYPSDIAVE WESNGQPENN YKTTPPVLDS DGSFFLYSRL TVDKSRWQEG

NVFSCSVMHE ALHNHYTQKS LSLSLGK

IgG1                                                                (SEQ ID NO: 5)
ASTKGPSVFPLAPSSKSTSGGTAALGCLVKDYFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPKDTLMISRTPEVTCVVVDVSHEDPEVKFNW

YVDGVEVHNAKTKPREECYNSTYRVVSVLTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFSCSVMHEALHN

HYTQKSLSLSPGK

IgG2                                                                (SEQ ID NO: 6)
ASTKGPSVFP LAPCSRSTSE STAALGCLVK DYFPEPVTVS WNSGALTSGV

HTFPAVLQSS GLYSLSSVVT VPSSNFGTQT YTCNVDHKPS NTKVDKTVER

KCCVECPPCP APPVAGPSVF LFPPKPKDTL MISRTPEVTC VVVDVSHEDP

EVQFNWYVDG VEVHNAKTKP REECFNSTFR VVSVLTVVHQ DWLNGKEYKC

KVSNKGLPAP IEKTISKTKG QPREPQVYTL PPSREEMTKN QVSLTCLVKG

FYPSDISVEW ESNGQPENNY KTTPPMLDSD GSFFLYSKLT VDKSRWQQGN

VFSCSVMHEA LHNHYTQKSL SLSPGK
```

IgG3 (SEQ ID NO: 7)

ASTKGPSVFP LAPCSRSTSG GTAALGCLVK DYFPEPVTVS WNSGALTSGV
HTFPAVLQSS GLYSLSSVVT VPSSSLGTQT YTCNVNHKPS NTKVDKRVEL
KTPLGDTTHT CPRCPEPKSC DTPPPCPRCP EPKSCDTPPP CPRCPEPKSC
DTPPPCPRCP APELLGGPSV FLFPPKPKDT LMISRTPEVT CVVVDVSHED
PEVQFKWYVD GVEVHNAKTK PREECYNSTF RVVSVLTVLH QDWLNGKEYK
CKVSNKALPA PIEKTISKTK GQPREPQVYT LPPSREEMTK NQVSLTCLVK
GFYPSDIAVE WESSGQPENN YNTTPPMLDS DGSFFLYSKL TVDKSRWQQG
NIFSCSVMHE ALHNRFTQKS LSLSPGK

IgG4 (SEQ ID NO: 8)

ASTKGPSVFP LAPCSRSTSE STAALGCLVK DYFPEPVTVS WNSGALTSGV
HTFPAVLQSS GLYSLSSVVT VPSSSLGTKT YTCNVDHKPS NTKVDKRVES
KYGPPCPSCP APEFLGGPSV FLFPPKPKDT LMISRTPEVT CVVVDVSQED
PEVQFNWYVD GVEVHNAKTK PREECFNSTY RVVSVLTVLH QDWLNGKEYK
CKVSNKGLPS SIEKTISKAK GQPREPQVYT LPPSQEEMTK NQVSLTCLVK
GFYPSDIAVE WESNGQPENN YKTTPPVLDS DGSFFLYSRL TVDKSRWQEG
NVFSCSVMHE ALHNHYTQKS LSLSLGK

IgG1 (SEQ ID NO: 9)

ASTKGPSVFPLAPSSKSTSGGTAALGCLVKDYFPEPVTVSWNSGALTSGVHTFPAVLQSSGLYSLSSVVTVPSSSLGTQTY
ICNVNHKPSNTKVDKKVEPKSCDKTHTCPPCPAPELLGGPCVFLFPPKPKDTLMISRTPEVTCVVVDVSHEDPEVKFNW
YVDGVEVHNAKTKPREECYNSTYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSVMHEALHN
HYTQKSLSLSPGK

IgG2 (SEQ ID NO: 10)

ASTKGPSVFP LAPCSRSTSE STAALGCLVK DYFPEPVTVS WNSGALTSGV
HTFPAVLQSS GLYSLSSVVT VPSSNFGTQT YTCNVDHKPS NTKVDKTVER
KCCVECPPCP APPVAGPCVF LFPPKPKDTL MISRTPEVTC VVVDVSHEDP
EVQFNWYVDG VEVHNAKTKP REECFNSTFR VVSVLTVVHQ DWLNGKEYKC
KVSNKGLPAP IEKTISKTKG QPREPQVYTL PPSREEMTKN QVSLTCLVKG
FYPSDISVEW ESNGQPENNY KTTPPMLDSD GSFFLYSKLT VDKSRWQQGN
VFSCSVMHEA LHNHYTQKSL SLSPGK

IgG3 (SEQ ID NO: 11)

ASTKGPSVFP LAPCSRSTSG GTAALGCLVK DYFPEPVTVS WNSGALTSGV
HTFPAVLQSS GLYSLSSVVT VPSSSLGTQT YTCNVNHKPS NTKVDKRVEL
KTPLGDTTHT CPRCPEPKSC DTPPPCPRCP EPKSCDTPPP CPRCPEPKSC
DTPPPCPRCP APELLGGPCV FLFPPKPKDT LMISRTPEVT CVVVDVSHED
PEVQFKWYVD GVEVHNAKTK PREECYNSTF RVVSVLTVLH QDWLNGKEYK
CKVSNKALPA PIEKTISKTK GQPREPQVYT LPPSREEMTK NQVSLTCLVK
GFYPSDIAVE WESSGQPENN YNTTPPMLDS DGSFFLYSKL TVDKSRWQQG
NIFSCSVMHE ALHNRFTQKS LSLSPGK

IgG4 (SEQ ID NO: 12)

ASTKGPSVFP LAPCSRSTSE STAALGCLVK DYFPEPVTVS WNSGALTSGV
HTFPAVLQSS GLYSLSSVVT VPSSSLGTKT YTCNVDHKPS NTKVDKRVES
KYGPPCPSCP APEFLGGPCV FLFPPKPKDT LMISRTPEVT CVVVDVSQED
PEVQFNWYVD GVEVHNAKTK PREECFNSTY RVVSVLTVLH QDWLNGKEYK
CKVSNKGLPS SIEKTISKAK GQPREPQVYT LPPSQEEMTK NQVSLTCLVK
GFYPSDIAVE WESNGQPENN YKTTPPVLDS DGSFFLYSRL TVDKSRWQEG
NVFSCSVMHE ALHNHYTQKS LSLSLGK

IgG1 (SEQ ID NO: 13)

ASTKGPSVFPLAPSSKSTSGGTAALGCLVKDYFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPKDTLMISRTPEVTCVVVDVSHEDPEVKFNW
YVDGVEVHNAKTKPRECQYNSTYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSVMHEALHN
HYTQKSLSLSPGK

IgG2 (SEQ ID NO: 14)

ASTKGPSVFP LAPCSRSTSE STAALGCLVK DYFPEPVTVS WNSGALTSGV
HTFPAVLQSS GLYSLSSVVT VPSSNFGTQT YTCNVDHKPS NTKVDKTVER
KCCVECPPCP APPVAGPSVF LFPPKPKDTL MISRTPEVTC VVVDVSHEDP
EVQFNWYVDG VEVHNAKTKP RECQFNSTFR VVSVLTVVHQ DWLNGKEYKC
KVSNKGLPAP IEKTISKTKG QPREPQVYTL PPSREEMTKN QVSLTCLVKG
FYPSDISVEW ESNGQPENNY KTTPPMLDSD GSFFLYSKLT VDKSRWQQGN
VFSCSVMHEA LHNHYTQKSL SLSPGK

IgG3 (SEQ ID NO: 15)

ASTKGPSVFP LAPCSRSTSG GTAALGCLVK DYFPEPVTVS WNSGALTSGV
HTFPAVLQSS GLYSLSSVVT VPSSSLGTQT YTCNVNHKPS NTKVDKRVEL
KTPLGDTTHT CPRCPEPKSC DTPPPCPRCP EPKSCDTPPP CPRCPEPKSC
DTPPPCPRCP APELLGGPSV FLFPPKPKDT LMISRTPEVT CVVVDVSHED
PEVQFKWYVD GVEVHNAKTK PRECQYNSTF RVVSVLTVLH QDWLNGKEYK
CKVSNKALPA PIEKTISKTK GQPREPQVYT LPPSREEMTK NQVSLTCLVK
GFYPSDIAVE WESSGQPENN YNTTPPMLDS DGSFFLYSKL TVDKSRWQQG
NIFSCSVMHE ALHNRFTQKS LSLSPGK

IgG4 (SEQ ID NO: 16)

ASTKGPSVFP LAPCSRSTSE STAALGCLVK DYFPEPVTVS WNSGALTSGV
HTFPAVLQSS GLYSLSSVVT VPSSSLGTKT YTCNVDHKPS NTKVDKRVES
KYGPPCPSCP APEFLGGPSV FLFPPKPKDT LMISRTPEVT CVVVDVSQED
PEVQFNWYVD GVEVHNAKTK PRECQFNSTY RVVSVLTVLH QDWLNGKEYK
CKVSNKGLPS SIEKTISKAK GQPREPQVYT LPPSQEEMTK NQVSLTCLVK
GFYPSDIAVE WESNGQPENN YKTTPPVLDS DGSFFLYSRL TVDKSRWQEG
NVFSCSVMHE ALHNHYTQKS LSLSLGK

-continued

IgG1 (SEQ ID NO: 17)
ASTKGPSVFPLAPSSKSTSGGTAALGCLVKDYFPEPVTVSWNSGALTSGVHTFPAVLQSSGLYSLSSVVTVPSSSLGTQTY
ICNVNHKPSNTKVDKKVEPKSCDKTHTCPPCPAPELLGGPCVFLFPPKPKDTLMISRTPEVTCVVVDVSHEDPEVKFNW
YVDGVEVHNAKTKPRECQYNSTYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSVMHEALHN
HYTQKSLSLSPGK

IgG2 (SEQ ID NO: 18)
ASTKGPSVFP LAPCSRSTSE STAALGCLVK DYFPEPVTVS WNSGALTSGV
HTFPAVLQSS GLYSLSSVVT VPSSNFGTQT YTCNVDHKPS NTKVDKTVER
KCCVECPPCP APPVAGPCVF LFPPKPKDTL MISRTPEVTC VVVDVSHEDP
EVQFNWYVDG VEVHNAKTKP RECQFNSTFR VVSVLTVVHQ DWLNGKEYKC
KVSNKGLPAP IEKTISKTKG QPREPQVYTL PPSREEMTKN QVSLTCLVKG
FYPSDISVEW ESNGQPENNY KTTPPMLDSD GSFFLYSKLT VDKSRWQQGN
VFSCSVMHEA LHNHYTQKSL SLSPGK

IgG3 (SEQ ID NO: 19)
ASTKGPSVFP LAPCSRSTSG GTAALGCLVK DYFPEPVTVS WNSGALTSGV
HTFPAVLQSS GLYSLSSVVT VPSSSLGTQT YTCNVNHKPS NTKVDKRVEL
KTPLGDTTHT CPRCPEPKSC DTPPPCPRCP EPKSCDTPPP CPRCPEPKSC
DTPPPCPRCP APELLGGPCV FLFPPKPKDT LMISRTPEVT CVVVDVSHED
PEVQFKWYVD GVEVHNAKTK PRECQYNSTF RVVSVLTVLH QDWLNGKEYK
CKVSNKALPA PIEKTISKTK GQPREPQVYT LPPSREEMTK NQVSLTCLVK
GFYPSDIAVE WESSGQPENN YNTTPPMLDS DGSFFLYSKL TVDKSRWQQG
NIFSCSVMHE ALHNRFTQKS LSLSPGK

IgG4 (SEQ ID NO: 20)
ASTKGPSVFP LAPCSRSTSE STAALGCLVK DYFPEPVTVS WNSGALTSGV
HTFPAVLQSS GLYSLSSVVT VPSSSLGTKT YTCNVDHKPS NTKVDKRVES
KYGPPCPSCP APEFLGGPCV FLFPPKPKDT LMISRTPEVT CVVVDVSQED
PEVQFNWYVD GVEVHNAKTK PRECQFNSTY RVVSVLTVLH QDWLNGKEYK
CKVSNKGLPS SIEKTISKAK GQPREPQVYT LPPSQEEMTK NQVSLTCLVK
GFYPSDIAVE WESNGQPENN YKTTPPVLDS DGSFFLYSRL TVDKSRWQEG
NVFSCSVMHE ALHNHYTQKS LSLSLGK

---

What is claimed is:

1. An antibody drug conjugate comprising an antibody comprising a heavy chain constant region in which position 295 by EU numbering is occupied by cysteine conjugated to a drug via the cysteine, wherein the heavy chain constant region has the sequence of any one of SEQ ID NOS:5-12 provided the C-terminal lysine can be absent.

2. The antibody drug conjugate of claim 1, wherein the heavy chain constant region has a cysteine at position 239 by EU numbering.

3. The antibody drug conjugate of claim 2, wherein the antibody is conjugated to the drug via both the cysteines at positions 295 and 239.

4. The antibody drug conjugate of claim 3, wherein the antibody is a heterodimer comprising two heavy chains and two light chains, wherein one molecule of the antibody is conjugated to four molecules of the drug via conjugation to the cysteine at position 295 and 239 in both heavy chains.

5. The antibody drug conjugate of claim 1, wherein the drug is a tubulysin.

6. The antibody drug conjugate of claim 5, wherein the drug is conjugated to the antibody via a glucuronide linker.

7. The antibody drug conjugate of claim 6, wherein the antibody is conjugated to a compound having a structure shown below providing the tubulysin and glucuronide linker:

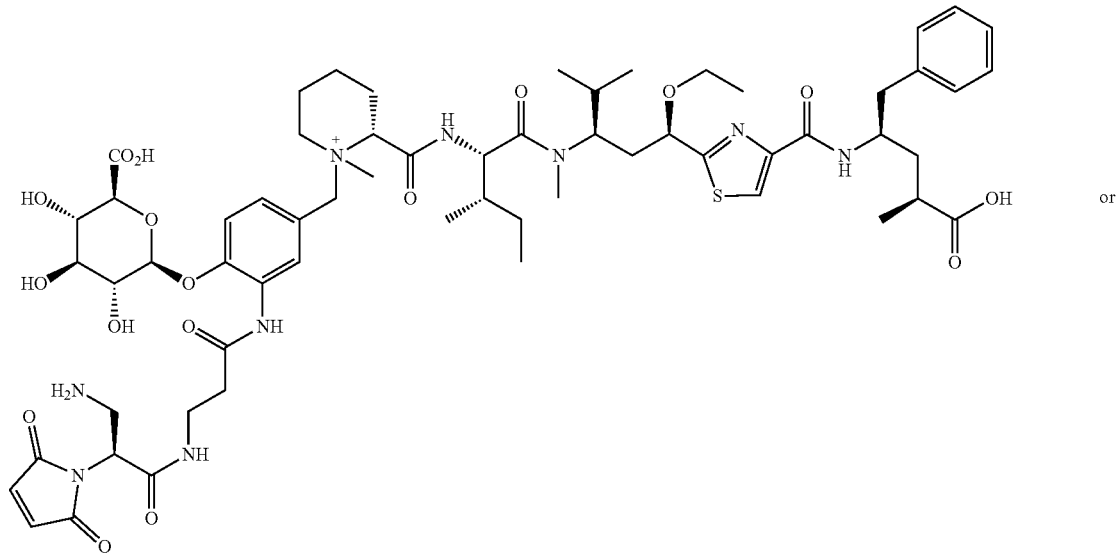

-continued

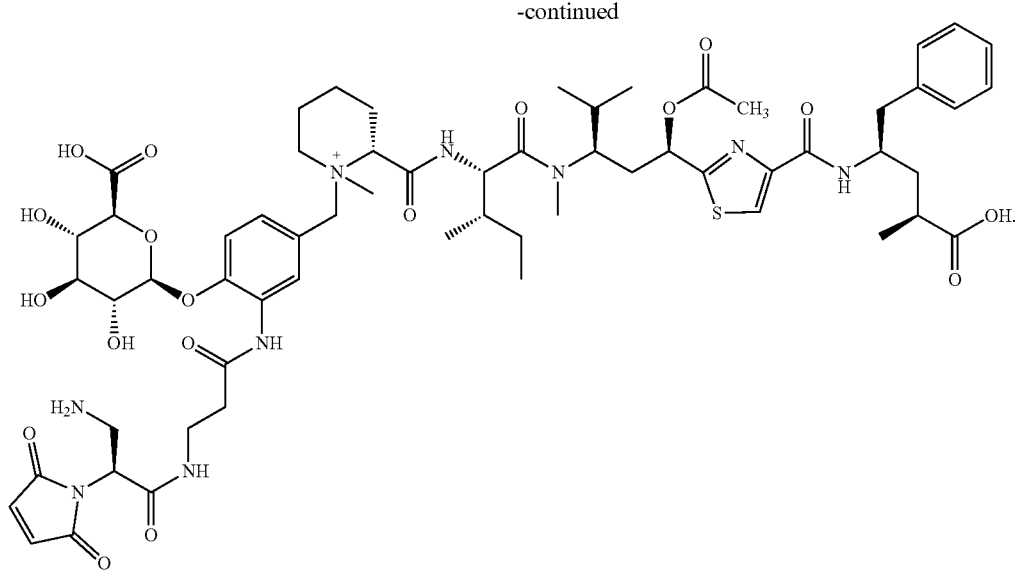

8. The antibody drug conjugate of claim 1, wherein the drug is MMAE, MMAF, or a minor groove binder.

9. The antibody drug conjugate of claim 1, wherein antibody is conjugated to the drug via a cleavable linker.

10. A pharmaceutical composition comprising the antibody drug conjugate of claim 1.

11. A method of producing an antibody drug conjugate comprising an antibody comprising a heavy chain constant region in which positions 239 and 295 by EU numbering are occupied by cysteines, wherein the heavy chain constant region comprises any one of SEQ ID NOS:9-12, the method comprising:
culturing a cell engineered to encode the antibody, wherein the antibody is expressed;
purifying the antibody; and
conjugating the antibody to a drug via the cysteines at position 239 and 295.

12. The method of claim 11, further comprising contacting the antibody with a reducing agent that inhibits formation of disulfide bonds between cysteines at positions 239 and 295.

13. The method of claim 12, wherein the antibody is contacted by including the reducing agent in a medium in which the antibody is cultured.

14. The method of claim 13, wherein the reducing agent is dithiothreitol, beta-mercaptoethanol or tris(2-carboxyethyl) phosphine.

15. The method of claim 14, wherein the reducing agent is dithiothreitol at a concentration of 0.1 to 2 mM.

* * * * *